US011540863B2

(12) United States Patent
Stoklund et al.

(10) Patent No.: US 11,540,863 B2
(45) Date of Patent: Jan. 3, 2023

(54) SPINAL SURGERY SYSTEMS AND METHODS

(71) Applicant: GetSet Surgical SA, Epalinges (CH)

(72) Inventors: Ole Stoklund, Lausanne (CH); Lawrence Binder, Miami, FL (US); John Kapitan, Leicester, NC (US)

(73) Assignee: GETSET SURGICAL SA ( * ) Notice: Subject to any disclaimer, the term of this patent is extended or adjusted under 35 U.S.C. 154(b) by 0 days.

(21) Appl. No.: 16/434,976

(22) Filed: Jun. 7, 2019

(65) Prior Publication Data
US 2020/0038064 A1    Feb. 6, 2020

Related U.S. Application Data

(60) Provisional application No. 62/712,938, filed on Jul. 31, 2018.

(51) Int. Cl.
A61B 17/70    (2006.01)
A61B 17/86    (2006.01)
(Continued)

(52) U.S. Cl.
CPC ...... A61B 17/7032 (2013.01); A61B 17/8615 (2013.01); A61B 17/8685 (2013.01); A61B 17/888 (2013.01); A61F 2/442 (2013.01); A61F 2/447 (2013.01); A61F 2/4611 (2013.01); A61B 17/7037 (2013.01); A61B 2017/564 (2013.01); A61F 2/4603 (2013.01);
(Continued)

(58) Field of Classification Search
CPC .. A61B 17/7032–7046; A61B 17/7082; A61B 17/8894
See application file for complete search history.

(56) References Cited

U.S. PATENT DOCUMENTS 2,905,178 A    9/1959 Hilzinger
3,681,840 A    8/1972 Pool
(Continued)

FOREIGN PATENT DOCUMENTS

CN    204033456 U    12/2014
GB    2348390 B    10/2000
(Continued)

OTHER PUBLICATIONS

International Search Report dated Oct. 15, 2019 for corresponding International Application No. PCT/2019/044429.
(Continued)

Primary Examiner — Eduardo C Robert
Assistant Examiner — Steven J Cotroneo
(74) Attorney, Agent, or Firm — David Meibos; Maywood IP Law

(57) ABSTRACT

A bone anchor system may include a bone anchor assembly and a driver tool. The bone anchor assembly may generally include a bone screw, a collar member, and a tulip member. The collar member may include first and second retaining arms configured to receive a retaining feature of the driver tool. The driver tool may be removably couplable to the bone anchor assembly by inserting the retention feature between the first and second retaining arms of the collar member, such that the retention feature is retained by the first and second retaining arms of the collar member.

24 Claims, 20 Drawing Sheets

(51) Int. Cl.
  *A61B 17/88* (2006.01)
  *A61F 2/44* (2006.01)
  *A61F 2/46* (2006.01)
  *A61B 17/56* (2006.01)
  *A61F 2/30* (2006.01)

(52) U.S. Cl.
  CPC .............. *A61F 2002/30112* (2013.01); *A61F 2002/30261* (2013.01); *A61F 2002/30593* (2013.01); *A61F 2002/4615* (2013.01); *A61F 2002/4627* (2013.01); *A61F 2002/4628* (2013.01)

(56) References Cited

U.S. PATENT DOCUMENTS

| | | |
|---|---|---|
| 3,703,843 A | 11/1972 | Laverty |
| RE28,111 E | 8/1974 | Laverty |
| 3,861,269 A | 1/1975 | Laverty |
| 4,268,253 A | 5/1981 | Gross et al. |
| 5,246,442 A | 9/1993 | Ashman et al. |
| 5,259,398 A | 11/1993 | Vrespa |
| 5,269,686 A | 12/1993 | James |
| 5,368,594 A | 11/1994 | Martin et al. |
| 5,405,328 A | 4/1995 | Vidal et al. |
| 5,593,410 A | 1/1997 | Vrespa |
| 5,601,553 A | 2/1997 | Trebing et al. |
| 5,672,176 A | 9/1997 | Biedermann et al. |
| 5,697,929 A | 12/1997 | Mellinger |
| 5,728,098 A | 3/1998 | Sherman et al. |
| 5,797,911 A | 8/1998 | Sherman et al. |
| 5,879,350 A | 3/1999 | Sherman et al. |
| 5,885,286 A | 3/1999 | Sherman et al. |
| 5,989,250 A | 11/1999 | Wagner et al. |
| 6,010,503 A | 1/2000 | Richelsoph et al. |
| 6,045,312 A | 4/2000 | Hsing |
| 6,053,917 A | 4/2000 | Sherman et al. |
| 6,179,841 B1 | 1/2001 | Jackson |
| 6,187,005 B1 | 2/2001 | Brace et al. |
| 6,189,422 B1* | 2/2001 | Stihl ................. A61B 17/8891 606/104 |
| 6,193,719 B1 | 2/2001 | Gournay et al. |
| 6,216,570 B1 | 4/2001 | Freed |
| 6,254,602 B1 | 7/2001 | Justis |
| 6,257,105 B1 | 7/2001 | Lin |
| 6,261,296 B1 | 7/2001 | Aebi et al. |
| 6,273,888 B1 | 8/2001 | Justis |
| 6,296,642 B1 | 10/2001 | Morrison et al. |
| 6,478,795 B1 | 11/2002 | Gournay et al. |
| 6,562,040 B1 | 5/2003 | Wagner |
| 6,660,006 B2 | 12/2003 | Markworth et al. |
| 6,712,825 B2 | 3/2004 | Aebi et al. |
| 6,743,233 B1 | 6/2004 | Baldwin et al. |
| 6,834,571 B1 | 12/2004 | Lowe et al. |
| 7,445,627 B2 | 11/2008 | Hawkes et al. |
| 7,476,226 B2 | 1/2009 | Weikel et al. |
| 7,476,239 B2 | 1/2009 | Jackson |
| 7,572,281 B2 | 8/2009 | Runco et al. |
| 7,677,891 B2 | 3/2010 | Niznick |
| 7,794,477 B2 | 9/2010 | Melkent et al. |
| 7,828,829 B2 | 11/2010 | Ensign |
| 8,029,285 B2 | 10/2011 | Holmen et al. |
| 8,088,163 B1 | 1/2012 | Kleiner |
| 8,226,656 B2 | 7/2012 | McBride |
| 8,235,997 B2 | 8/2012 | Hoffman et al. |
| 8,241,294 B2 | 8/2012 | Sommerich et al. |
| 8,343,165 B2* | 1/2013 | Berrevoets ......... A61B 17/8875 606/104 |
| 8,608,651 B2 | 12/2013 | Shluzas |
| 8,668,699 B2 | 3/2014 | Thomas et al. |
| 8,685,029 B2 | 4/2014 | Dziedzic et al. |
| 8,828,060 B2 | 9/2014 | Biedermann et al. |
| 8,900,240 B2 | 12/2014 | White et al. |
| 8,920,424 B2 | 12/2014 | Boykin |
| 8,968,367 B2 | 3/2015 | Kretzer et al. |
| 8,986,307 B2 | 3/2015 | Kirschman |
| 9,050,062 B1 | 6/2015 | Gauthier et al. |
| 9,078,679 B2 | 7/2015 | Schuele et al. |
| 9,084,642 B2 | 7/2015 | Peultier |
| 9,168,058 B2 | 10/2015 | Duperier et al. |
| 9,198,695 B2 | 12/2015 | Shluzas et al. |
| 9,289,249 B2* | 3/2016 | Ramsay ............. A61B 17/7076 |
| 9,295,500 B2* | 3/2016 | Marigowda ........ A61B 17/7082 |
| 9,339,319 B2 | 5/2016 | Schmuck et al. |
| 9,345,587 B2 | 5/2016 | Mitchell |
| 9,358,060 B2* | 6/2016 | Jerke ................. A61B 17/8875 |
| 9,393,039 B2 | 7/2016 | Lechner et al. |
| 9,446,507 B2 | 9/2016 | Nino et al. |
| 9,463,063 B2 | 10/2016 | Seddon et al. |
| 9,532,814 B2 | 1/2017 | Harper |
| 9,572,617 B1 | 2/2017 | Prado et al. |
| RE46,409 E | 5/2017 | Foley et al. |
| 9,642,654 B2* | 5/2017 | Reimels ............. A61B 17/7082 |
| 9,649,140 B1* | 5/2017 | Doose ................ A61B 17/7089 |
| 9,693,814 B2 | 7/2017 | Schaller et al. |
| 9,855,087 B2* | 1/2018 | Divincenzo ........ A61B 17/8875 |
| 2002/0091386 A1 | 7/2002 | Martin et al. |
| 2002/0138076 A1 | 9/2002 | Biedermann et al. |
| 2003/0060714 A1 | 3/2003 | Henderson et al. |
| 2003/0125741 A1 | 7/2003 | Biedermann et al. |
| 2004/0082956 A1 | 4/2004 | Baldwin et al. |
| 2004/0138662 A1* | 7/2004 | Landry ............. A61B 17/7037 606/86 A |
| 2004/0181224 A1 | 9/2004 | Biedermann et al. |
| 2006/0149241 A1 | 7/2006 | Richelsoph et al. |
| 2006/0241599 A1 | 10/2006 | Konieczynski et al. |
| 2007/0213737 A1 | 9/2007 | Schermerhorn et al. |
| 2008/0015584 A1 | 1/2008 | Richelsoph |
| 2008/0027544 A1 | 1/2008 | Melkent |
| 2008/0045970 A1* | 2/2008 | Saidha ............... A61B 17/7082 606/104 |
| 2008/0065219 A1 | 3/2008 | Dye |
| 2009/0005814 A1* | 1/2009 | Miller ................ A61B 17/7085 606/246 |
| 2009/0018591 A1 | 1/2009 | Hawkes et al. |
| 2009/0054991 A1 | 2/2009 | Biyani et al. |
| 2009/0234395 A1* | 9/2009 | Hoffman ............ A61B 17/8875 606/86 A |
| 2009/0259234 A1 | 10/2009 | Waller |
| 2009/0264895 A1* | 10/2009 | Gasperut ........... A61B 17/7098 606/104 |
| 2010/0137879 A1 | 6/2010 | Ko et al. |
| 2010/0198272 A1* | 8/2010 | Keyer ................ A61B 17/7082 606/302 |
| 2010/0241175 A1 | 9/2010 | Walker et al. |
| 2011/0046637 A1 | 2/2011 | Patel et al. |
| 2011/0077694 A1 | 3/2011 | Biedermann et al. |
| 2011/0208238 A1 | 8/2011 | Hoffman |
| 2011/0213424 A1* | 9/2011 | Biedermann ...... A61B 17/7037 606/305 |
| 2011/0313471 A1* | 12/2011 | McLean ............. A61B 17/7082 606/305 |
| 2012/0143224 A1 | 6/2012 | Chan |
| 2012/0143265 A1 | 6/2012 | Biedermann et al. |
| 2013/0096568 A1 | 4/2013 | Justis |
| 2013/0096618 A1 | 4/2013 | Chandanson et al. |
| 2013/0103102 A1 | 4/2013 | Taylor et al. |
| 2013/0123923 A1 | 5/2013 | Pavlov et al. |
| 2013/0253517 A1 | 9/2013 | Mitchell et al. |
| 2013/0253518 A1 | 9/2013 | Mitchell et al. |
| 2013/0253519 A1 | 9/2013 | Mitchell et al. |
| 2013/0253594 A1 | 9/2013 | Zucherman et al. |
| 2013/0253595 A1 | 9/2013 | Zucherman et al. |
| 2013/0261626 A1 | 10/2013 | Chavarria et al. |
| 2014/0025119 A1 | 1/2014 | Biedermann et al. |
| 2014/0031880 A1 | 1/2014 | Biedermann et al. |
| 2014/0058465 A1 | 2/2014 | Nichols et al. |
| 2014/0277212 A1 | 9/2014 | Dauster |
| 2015/0148835 A1 | 5/2015 | Faller et al. |
| 2015/0265271 A1 | 9/2015 | Galligan et al. |
| 2016/0030188 A1 | 2/2016 | Lynn et al. |
| 2016/0175060 A1 | 6/2016 | Park |
| 2016/0296344 A1 | 10/2016 | Greenhalgh et al. |

(56) References Cited

U.S. PATENT DOCUMENTS

2018/0235684 A1* 8/2018 Hawkes ............. A61B 17/7082
2019/0029737 A1* 1/2019 Wall ....................... A61B 17/86
2020/0315666 A1* 10/2020 Nichols ................ A61B 17/888

FOREIGN PATENT DOCUMENTS

| WO | WO2007038654 | 4/2007 |
| WO | WO2009015100 | 1/2009 |
| WO | WO2009040840 | 4/2009 |
| WO | WO2016073912 | 5/2016 |

OTHER PUBLICATIONS

International Search Report dated Oct. 15, 2019 for corresponding International Application No. PCT/2019/044456.

* cited by examiner

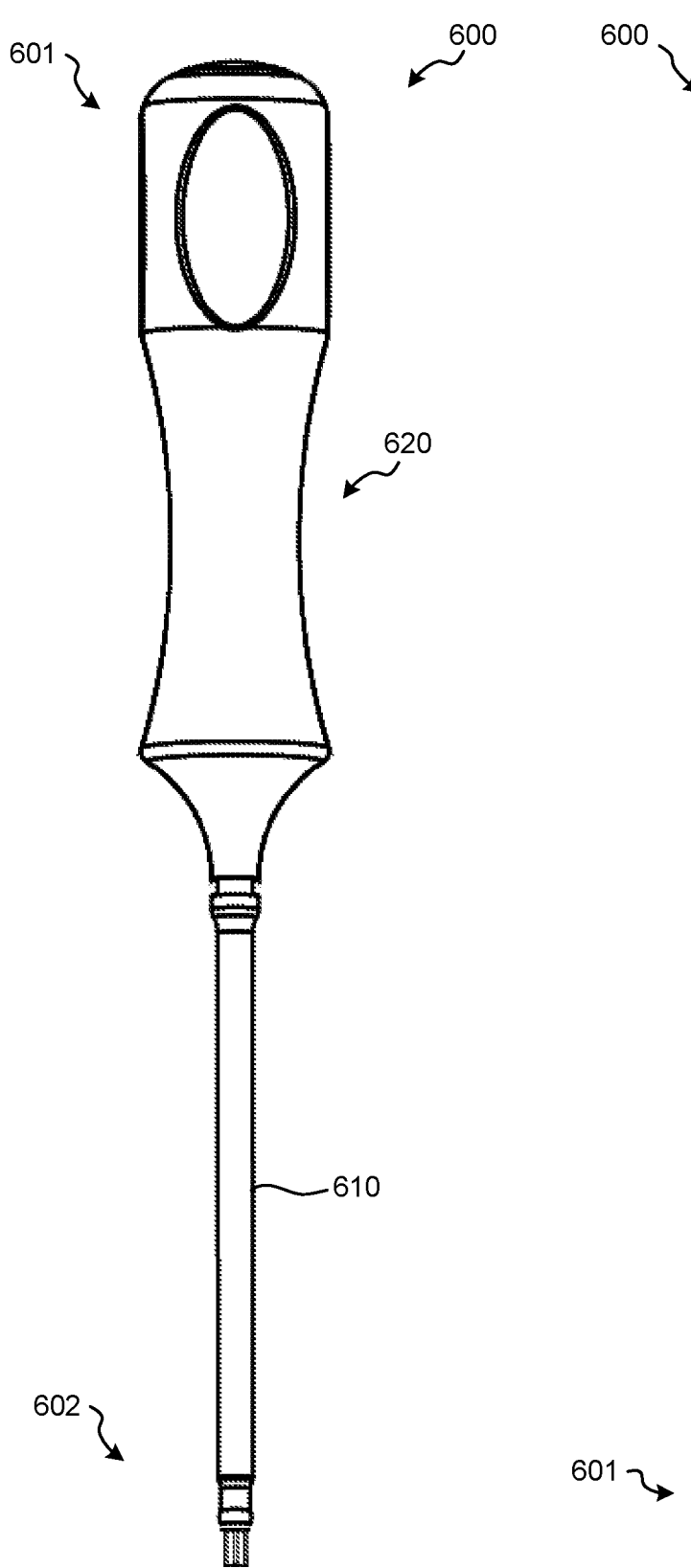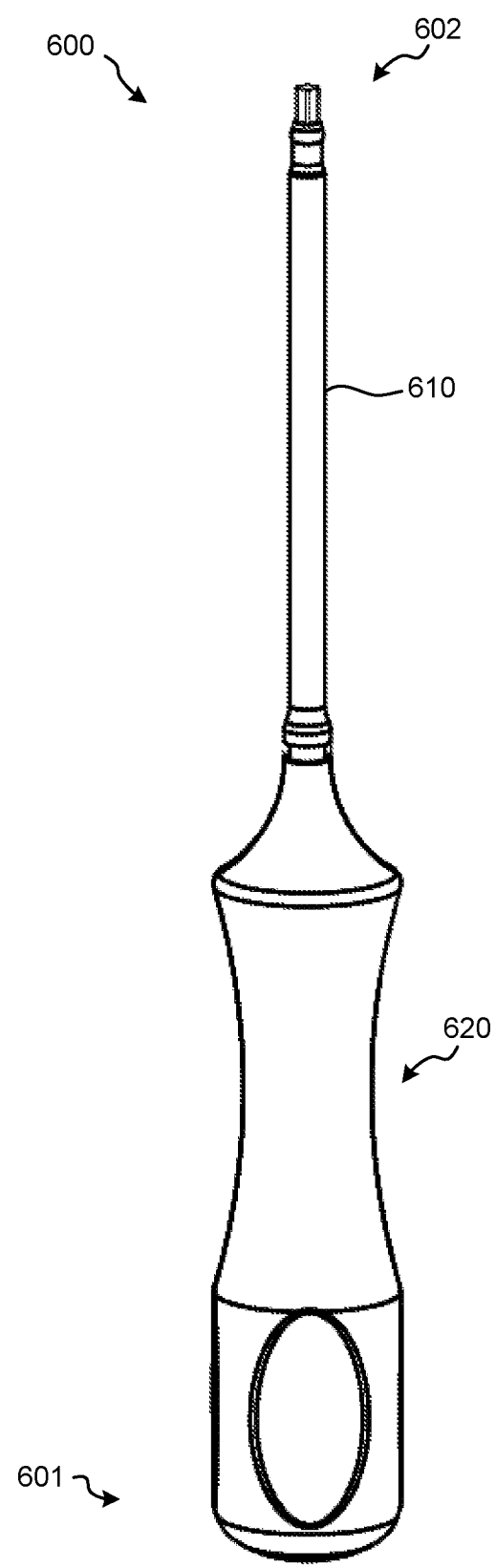
FIG. 6B  FIG. 6C

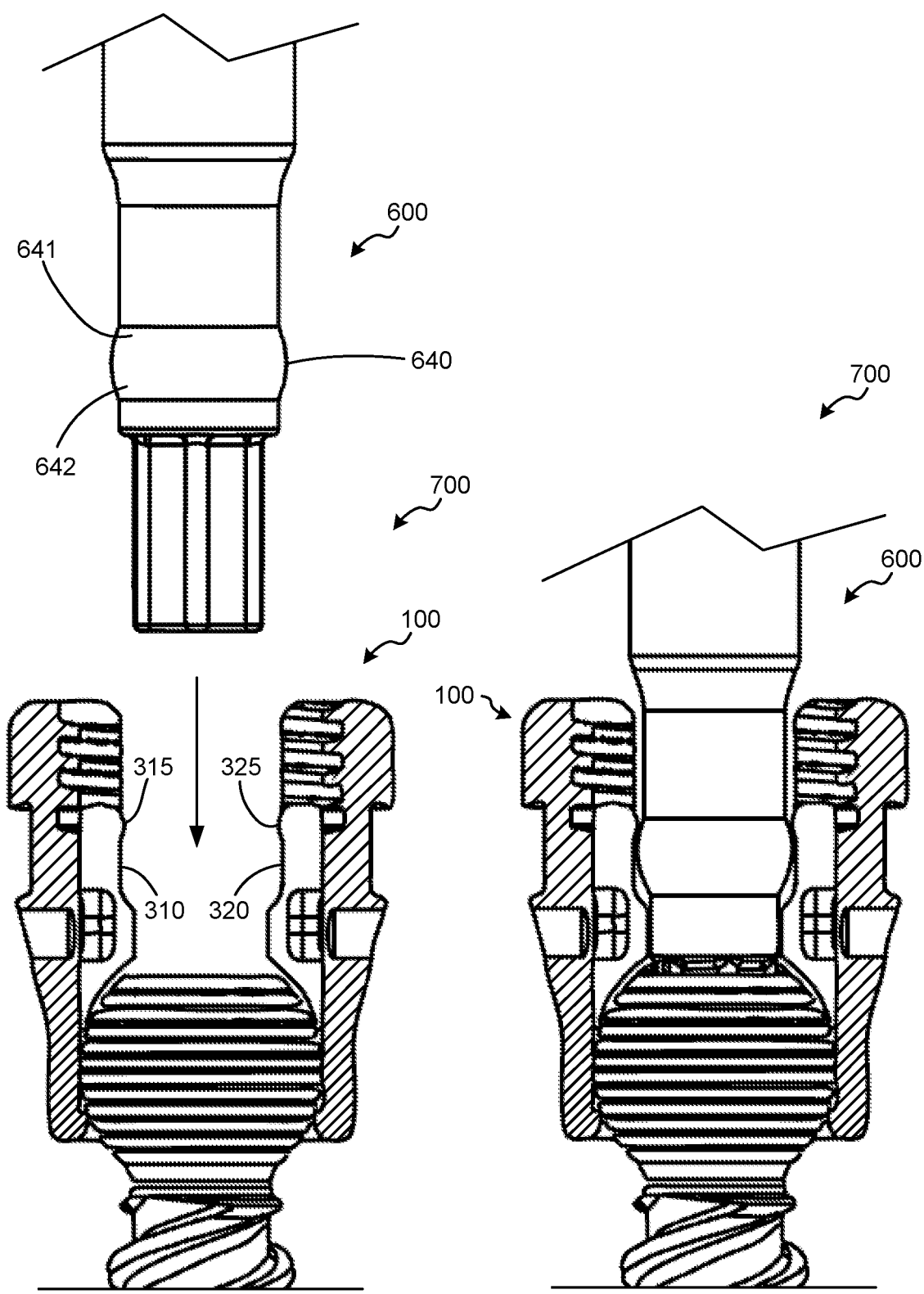
FIG. 7A  FIG. 7B

SPINAL SURGERY SYSTEMS AND METHODS

CROSS-REFERENCE TO RELATED APPLICATIONS

This application claims the benefit of U.S. Provisional Patent Application No. 62/712,938 filed on Jul. 31, 2018, entitled "SPINAL SURGERY SYSTEMS AND METHODS," the disclosure of which is incorporated herein by reference in its entirety.

TECHNICAL FIELD

The present disclosure relates to surgical systems, methods, instruments, and devices. More specifically, the present disclosure relates to improved surgical systems, methods, instruments, and devices for implanting bone anchor assemblies in a bone of a patient.

BACKGROUND

Spinal fixation procedures utilizing pedicle screws and rod-based fixation assemblies can be used to correct spinal conditions such as degenerative disc disease, spondylolisthesis, spinal deformities, or other spinal conditions through minimally invasive or invasive spinal surgery. For example, two or more bone anchor assemblies may be secured into bone structures of a patient's vertebrae with connecting rods secured between adjacent bone anchor assemblies in order to stabilize one or more vertebral joints of a patient. These connecting rods typically run longitudinally along the length of the patient's spine between adjacent bone anchor assemblies. However, connecting rods can be arranged in a variety of positions and/or configurations (including the use of multiple connecting rods and/or cross-bars, where desired) in view of a patient's specific anatomy and/or a specific spinal correction.

Unfortunately, the process of implanting a bone anchor assembly with a suitable driver tool can be difficult when the bone anchor assembly is not sufficiently secured to the driver tool. Accordingly, improved surgical systems, methods, instruments, and devices that reduce or eliminate this characteristic would be desirable.

SUMMARY

The various systems and methods of the present disclosure have been developed in response to the present state of the art, and in particular, in response to the problems and needs in the art that have not yet been fully solved by currently available surgical instruments, devices, systems, and methods for implanting bone anchor assemblies in a patient.

According to some embodiments, a bone anchor system may include a bone anchor assembly and a driver tool. The bone anchor assembly may include a bone screw, a collar member, and a tulip member. The bone screw may have a shank, external threading along the shank configured to engage bone, and a bone screw head coupled to a proximal end of the shank. The bone screw head may also include a driver engagement feature. The collar member may have a posterior end, an anterior end, first and second retaining arms projecting from the posterior end of the collar member, a receptacle configured to receive the bone screw head at any of a range of relative orientations, about multiple orthogonal axes of rotation, and a grip feature proximate the receptacle, the receptacle and grip feature configured to engage the bone screw head. The tulip member may include a posterior end, an anterior end, an internal bore, first and second tulip arms proximate the posterior end of the tulip member, and a transverse channel formed between the first and second tulip arms. The driver tool may include an elongate shaft having a proximal and distal ends and a bone screw engagement feature located at the distal end of the elongate shaft, such that the bone screw engagement feature is engageable with the driver engagement feature of the bone screw head to facilitate rotation of the bone screw with the driver tool. The driver tool may also include a retention feature located proximate the bone screw engagement feature. The driver tool may be removably couplable to the bone anchor assembly by inserting the retention feature between the first and second retaining arms of the collar member such that the retention feature is retained by the first and second retaining arms.

In other embodiments, a driver tool may include an elongate shaft having proximal and distal ends, a bone screw engagement feature located at the distal end of the elongate shaft, and a retention feature located along the elongate shaft, proximal to the bone screw engagement feature. The retention feature may be configured to removably couple the driver tool to a bone anchor assembly as the bone screw engagement feature is moved into engagement with a driver engagement feature of a bone screw of the bone anchor assembly.

In yet other embodiments, a method for implanting a bone anchor assembly through use of a driver tool having an elongate shaft having a proximal end, a distal end, a bone screw engagement feature located at the distal end of the elongate shaft, and a retention feature that is located proximal the bone screw engagement feature may include aligning the bone screw engagement feature with a driver engagement feature of the bone anchor assembly. The method may also include moving the bone screw engagement feature into engagement with the driver engagement feature, engaging the retention feature with the bone anchor assembly such that, with the bone screw engagement feature in engagement with the driver engagement feature, the retention feature is removably coupled to the bone anchor assembly, and inserting the bone anchor assembly, coupled to the driver tool, into a surgical site of a patient.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 6B is a left side view of the driver tool 600 of FIG. 6A;

FIG. 6C is a right side view of the driver tool 600 of FIG. 6A;

FIG. 7A is a bone anchor system 700 including a driver tool 600 and a bone anchor assembly 100, prior to coupling the driver tool 600 to the bone anchor assembly 100;

FIG. 7B is the bone anchor system 700 of FIG. 7A with the driver tool 600 coupled to the bone anchor assembly 100;

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
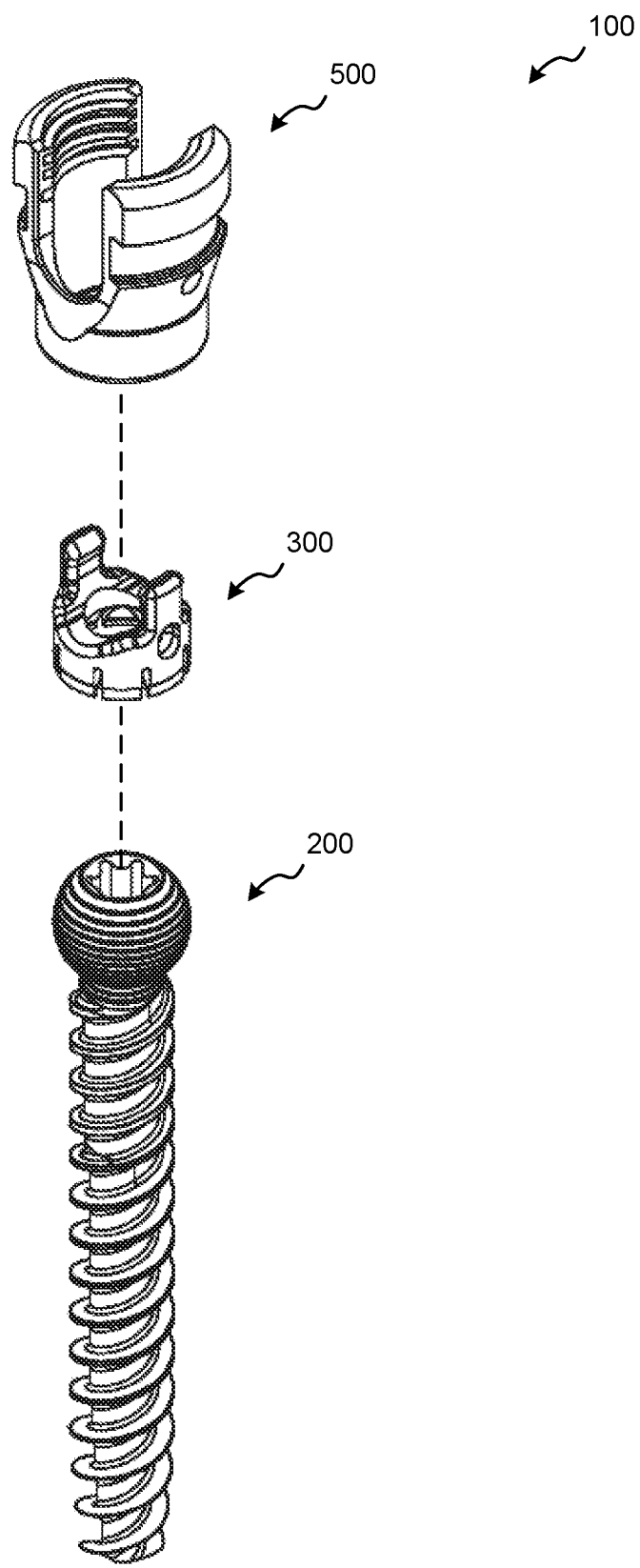
FIG. 1 is an exploded view of a bone anchor assembly 100, according to an embodiment of the present disclosure.

FIG. 1 illustrates an exploded view of a bone anchor assembly 100, according to an embodiment of the present disclosure. The bone anchor assembly 100 may generally include a bone screw 200, a collar member 300, and a tulip member 500. The collar member 300 and the tulip member 500 may each include grip features configured to engage and couple each of the collar member 300 and the tulip member to the head of the bone screw 200, as will be discussed in more detail below.

Figure 2A:
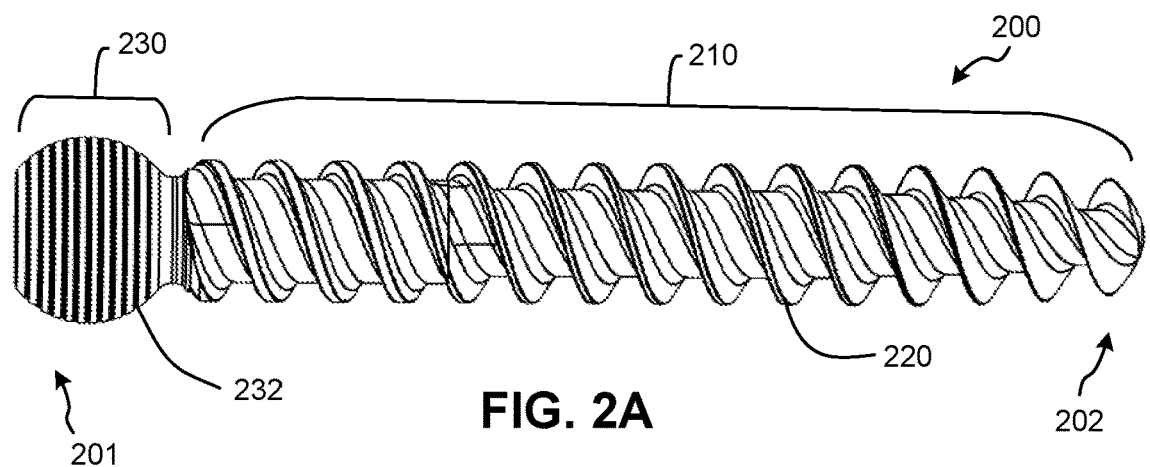
FIG. 2A is a side view of a bone screw 200, according to an embodiment of the present disclosure.
Figure 2B:
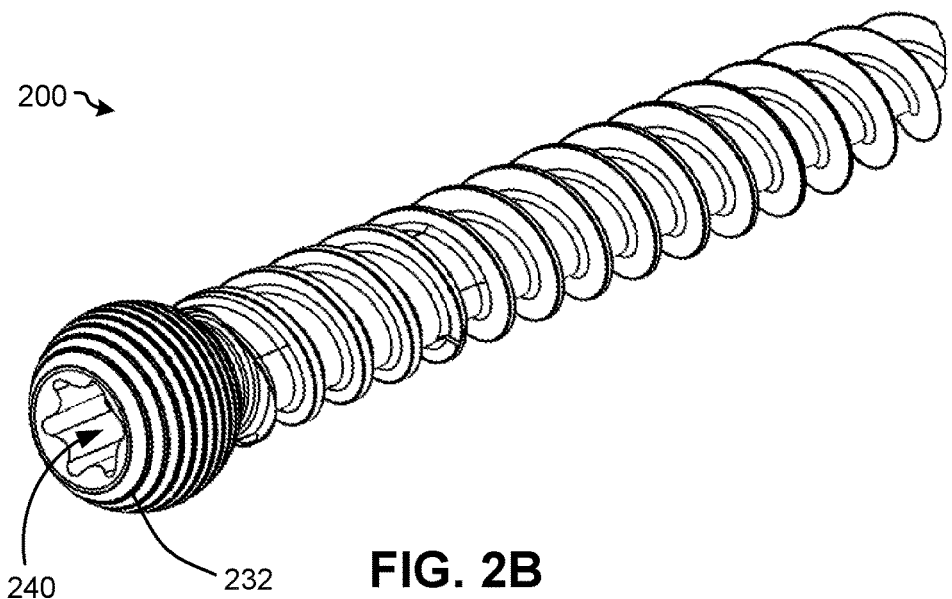
FIG. 2B is a perspective view of the bone screw 200 of FIG. 2A.
Figure 2C:
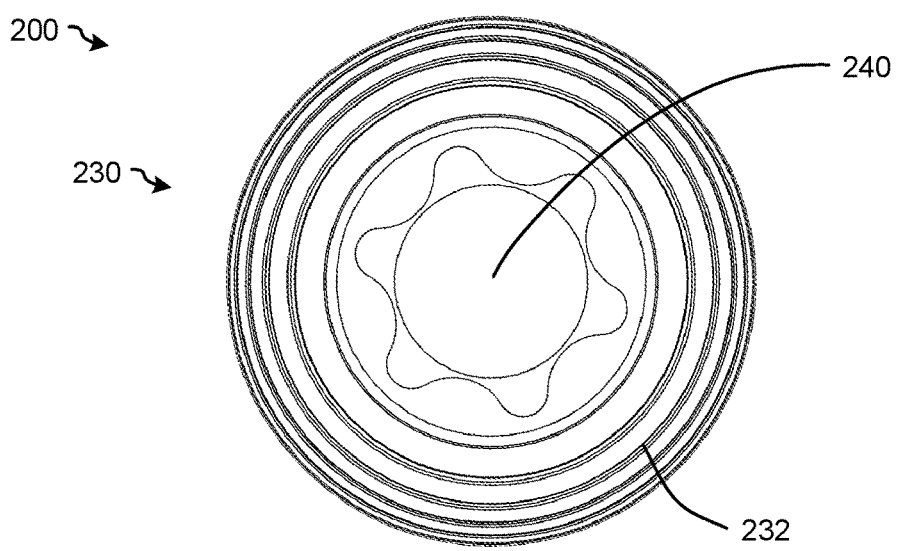
FIG. 2C is a top view of the bone screw 200 of FIG. 2A.

FIGS. 2A-2C illustrate various views of a bone screw 200, according to an embodiment of the present disclosure. Specifically, FIG. 2A is a side view of the bone screw 200; FIG. 2B is a perspective view of the bone screw 200; and FIG. 2C is a top view of the bone screw 200. The bone screw 200 may generally include a proximal end 201, a distal end 202, a shank 210 extending between the proximal and distal ends 201, 202 of the bone screw 200, external threading 220 arranged along the shank 210 and configured to engage bone, as well as a bone screw head 230 coupled to the proximal end 201 of the bone screw 200.

In at least one embodiment, the bone screw head 230 may be polyaxial including a semispherical shape and one or more horizontal ridges 232 formed around a circumference of the bone screw head 230. However, it will be understood that any size, shape, or style of bone screw head 230 may also be used.

The bone screw head 230 may also include a driver engagement feature 240 formed in the bone screw head 230. In at least one embodiment, the driver engagement feature 240 may have an internal hexalobular shape. However, it will be understood that any suitable size, shape, or style of driver engagement feature 240 may also be used in conjunction with the teachings of the present disclosure.

Figure 3A:
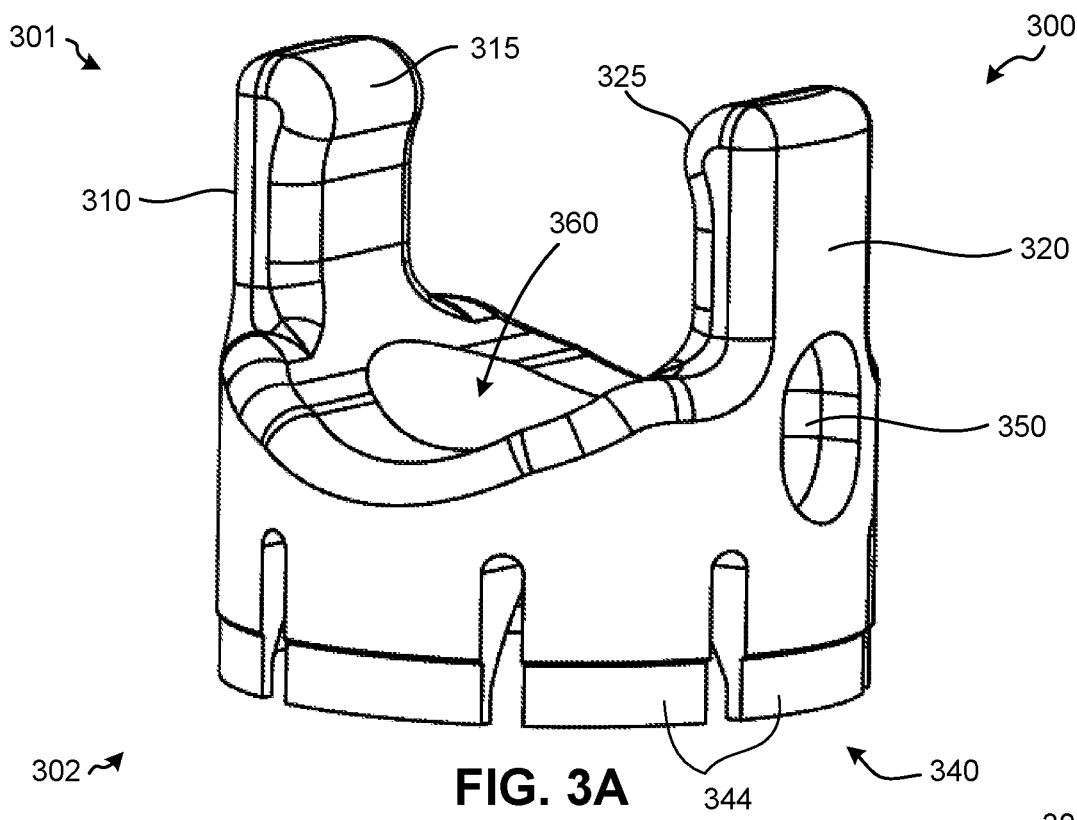
FIG. 3A is a top perspective view of a collar member 300, according to an embodiment of the present disclosure.
Figure 3B:
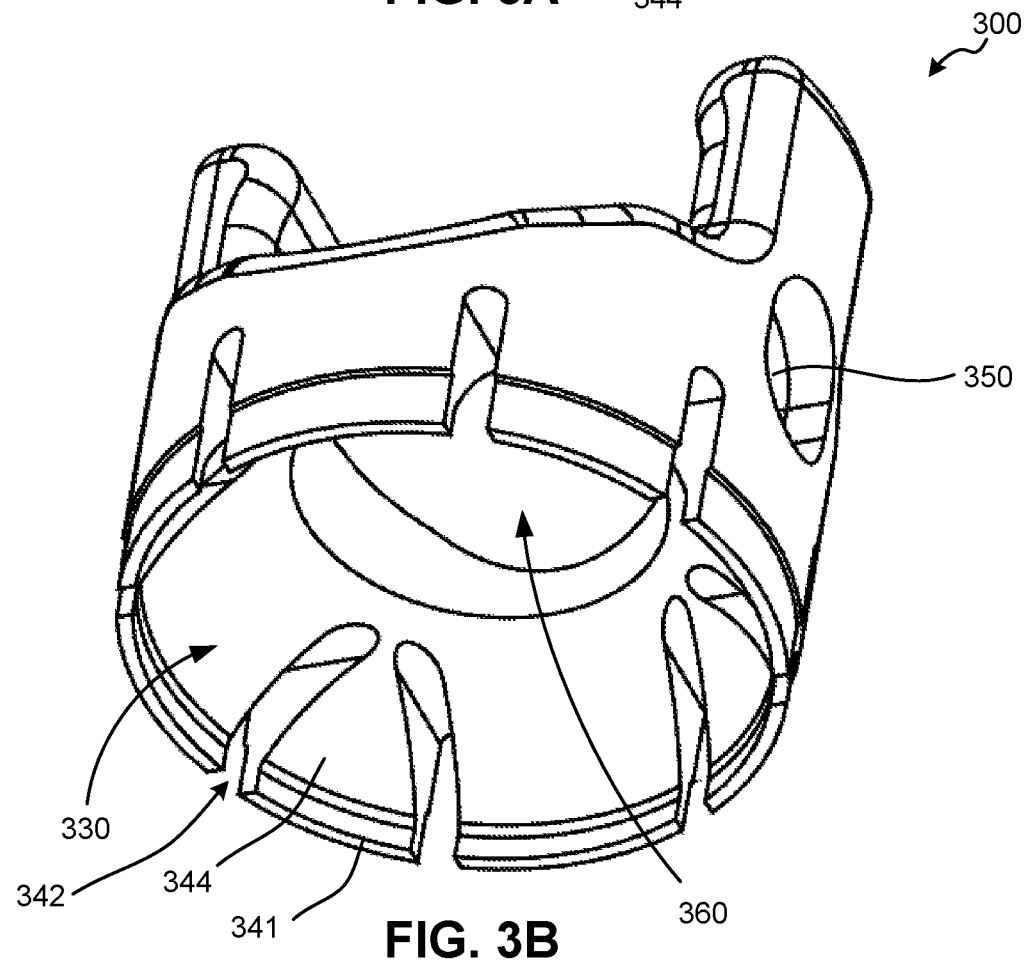
FIG. 3B is a bottom perspective view of the collar member 300 of FIG. 3A.
Figure 3C:
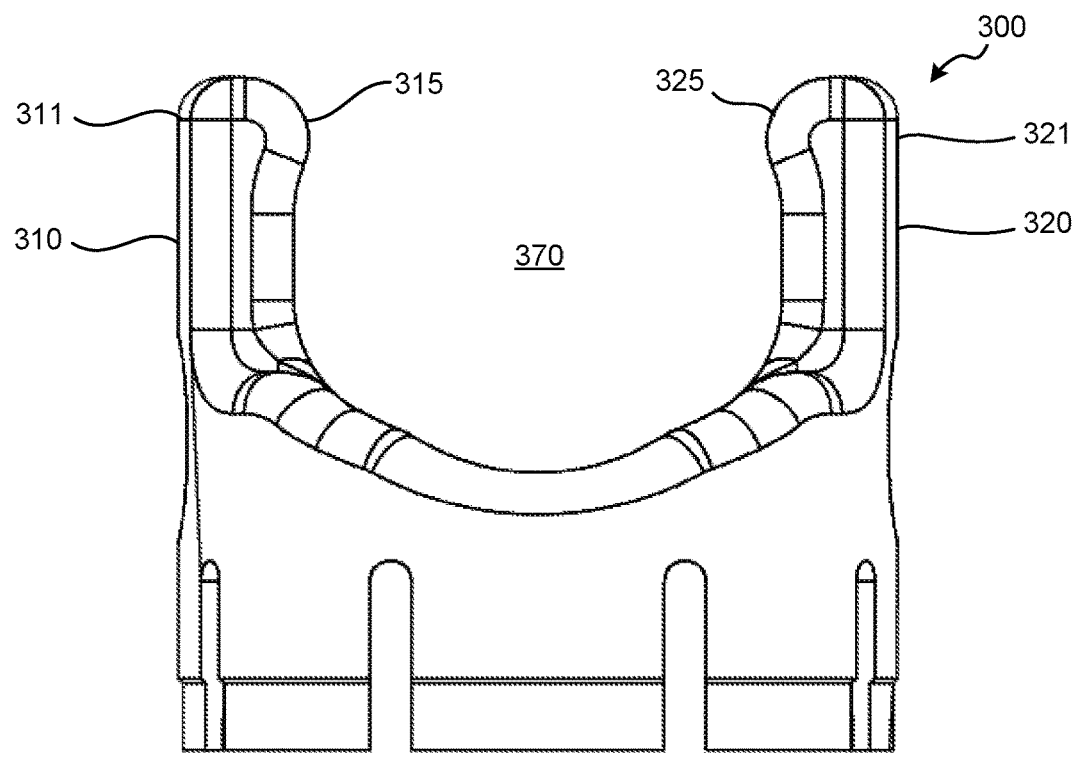
FIG. 3C is a front side view of the collar member 300 of FIG. 3A.
Figure 3D:
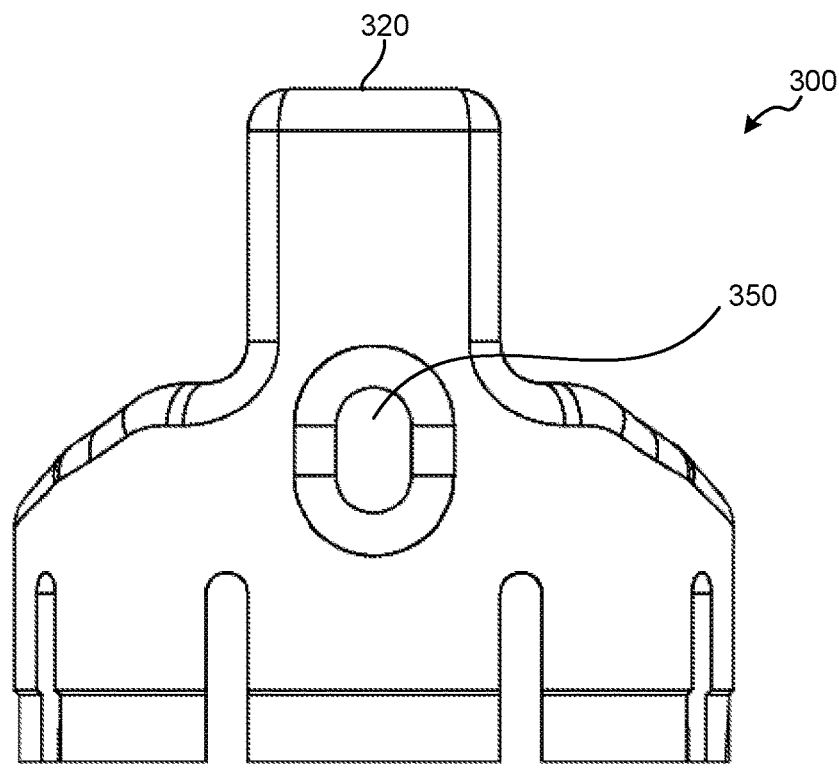
FIG. 3D is a left side view of the collar member 300 of FIG. 3A.
Figure 3E:
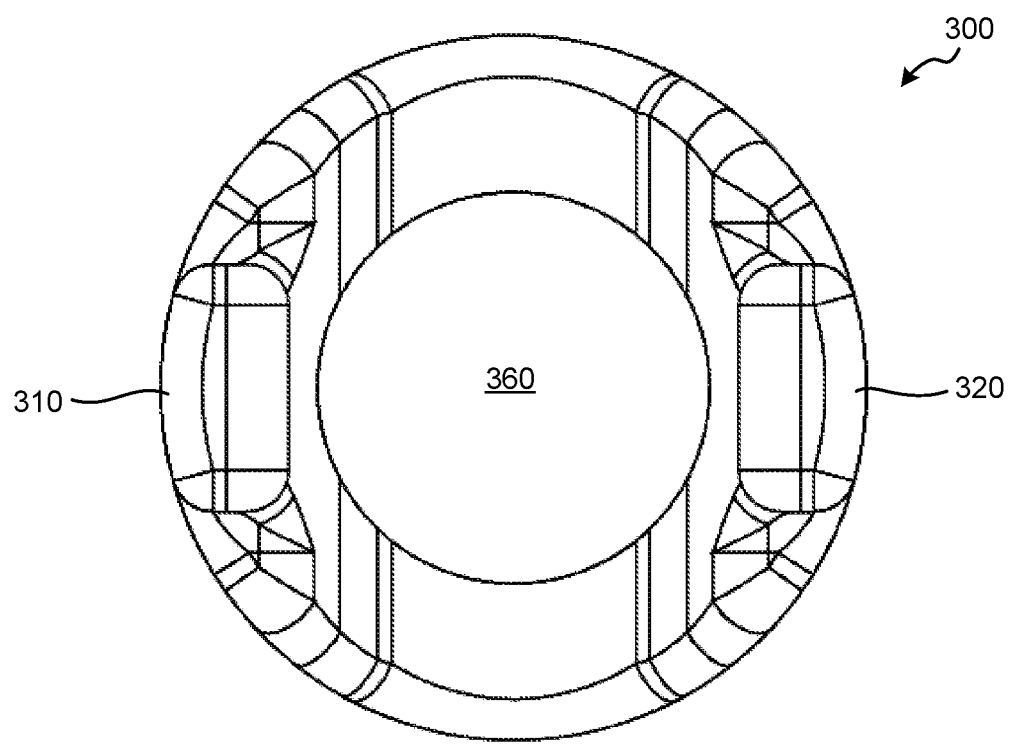
FIG. 3E is a top view of the collar member 300 of FIG. 3A.
Figure 3F:
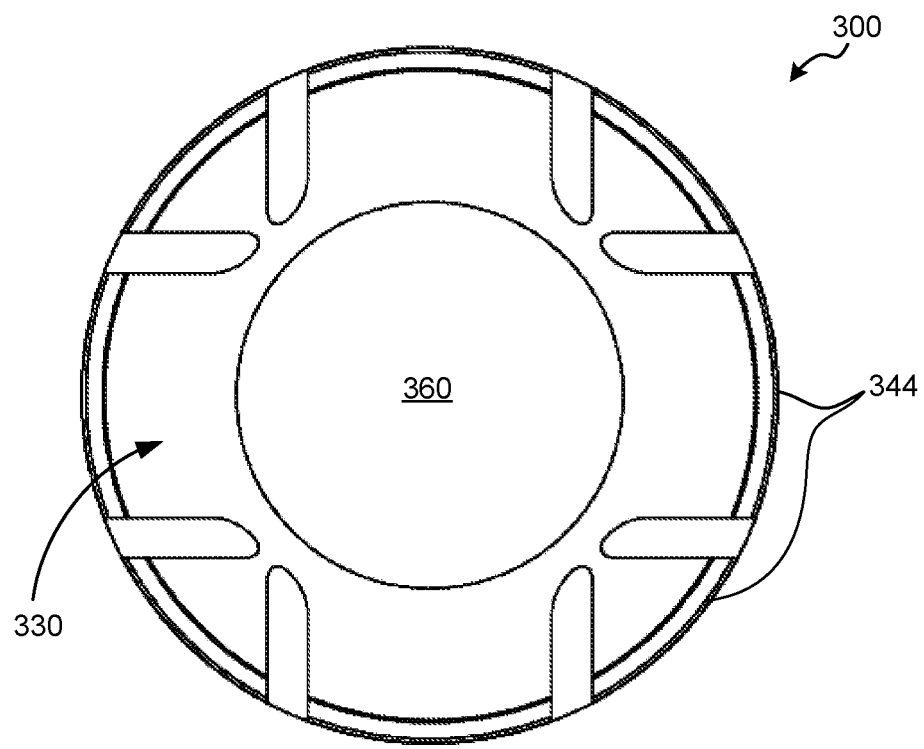
FIG. 3F is a bottom view of the collar member 300 of FIG. 3A.

FIGS. 3A-3F illustrate various views of a collar member 300, according to an embodiment of the present disclosure. Specifically, FIG. 3A is a top perspective view of the collar member 300; FIG. 3B is a bottom perspective view of the collar member 300; FIG. 3C is a front side view of the collar member 300; FIG. 3D is a left side view of the collar member 300; FIG. 3E is a top view of the collar member 300; and FIG. 3F is a bottom view of the collar member 300. The collar member 300 may generally include a posterior end 301, an anterior end 302, a first retaining arm 310, a second retaining arm 320, a receptacle 330 formed in the anterior end 302 of the collar member 300, and a grip feature 340 protruding from the anterior end 302 of the collar member 300.

The first and second retaining arms 310, 320 may each project from the posterior end 301 of the collar member 300 on opposite sides of the posterior end 301 of the collar member 300. The first retaining arm 310 may include a first retaining tab 315 located on a posterior end 311 of the first retaining arm 310, and the second retaining arm 320 may include a second retaining tab 325 located on a posterior end 321 of the second retaining arm 320, opposite the first retaining tab 315. The first and second retaining tabs 315, 325 may each project toward each other and into a space 370 formed between the first and second retaining arms 310, 320. In at least one embodiment, the first and second retaining arms 310, 320 may be resilient such that they may bend and flex away from each other when a force is applied to the first and second retaining arms 310, 320, as will be discussed in more detail below. However, it will also be understood that in other embodiments, the first and second retaining arms 310, 320 may be rigid and/or substantially inflexible.

The receptacle 330 formed in the anterior end 302 of the collar member 300 may be configured to receive and engage the bone screw head 230 at any of a range of relative orientations, about multiple orthogonal axes of rotation. In at least one embodiment, the receptacle 330 may have a semispherical shape that is complementary to the shape of the bone screw head 230. However, it will be understood that the receptacle 330 may have any suitable size, shape, or style that may interact with any corresponding size, shape, or style of bone screw head 230.

Figure 4:
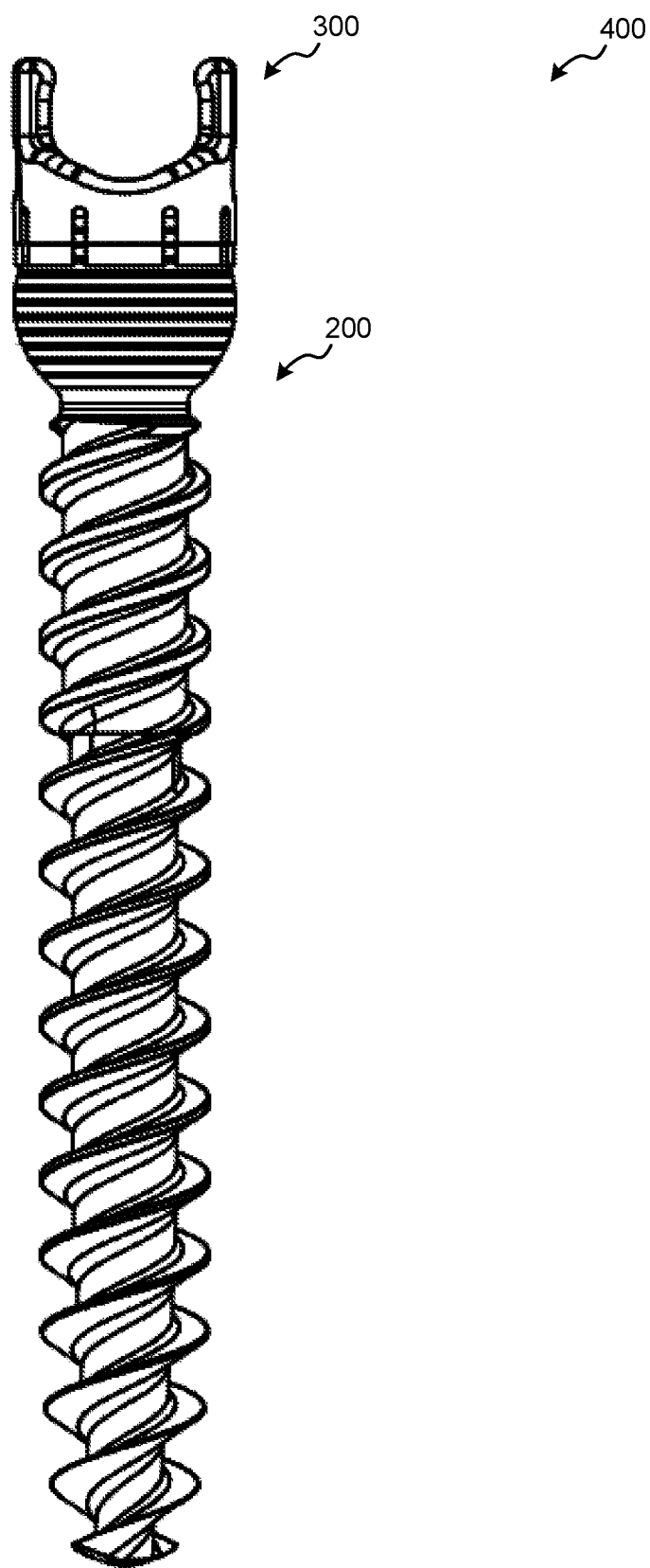
FIG. 4 is a front side view of a partial bone anchor assembly 400 including the bone screw 200 of FIG. 2A coupled to the collar member 300 of FIG. 3A.

The grip feature 340 may be proximate the receptacle 330 and configured to engage the bone screw head 230. In at least one embodiment, the grip feature 340 may comprise a collet structure with one or more collet arms 344 projecting from the anterior end 302 of the collar member 300. The one or more collet arms 344 may be resilient and/or separated from each other by one or more gaps 342. The one or more collet arms 344 may be arranged about the receptacle 330 and/or at least partially encircle the receptacle 330. Each of the one or more collet arms 344 may further include an edge 341 configured to grip the one or more horizontal ridges 232 formed in the bone screw head 230. In this manner, the collar member 300 may engage the bone screw head 230 at any of a range of relative orientations, about multiple orthogonal axes of rotation. For example, FIG. 4 illustrates a partial bone anchor assembly 400 comprising the bone screw 200 coupled to the collar member 300 via the one or more collet arms 344 that project from the anterior end 302 of the collar member 300.

The collar member 300 may include a central aperture 360 extending through the collar member 300 between the posterior and anterior ends 301, 302 of the collar member 300. The central aperture 360 may be configured to receive a driver tool therethrough, as will be explained in more detail below with respect to FIGS. 7A and 7B.

The collar member 300 may also include collar depressions 350 formed in the sides of the collar member 300 proximate the first and second retaining arms 310, 320. The collar depressions 350 may interact with the tulip member 500 to facilitate coupling of the tulip member 500 to the collar member 300, as will also be discussed in more detail below with respect to FIGS. 5A-5F and 7A-7B.

Figure 5A:
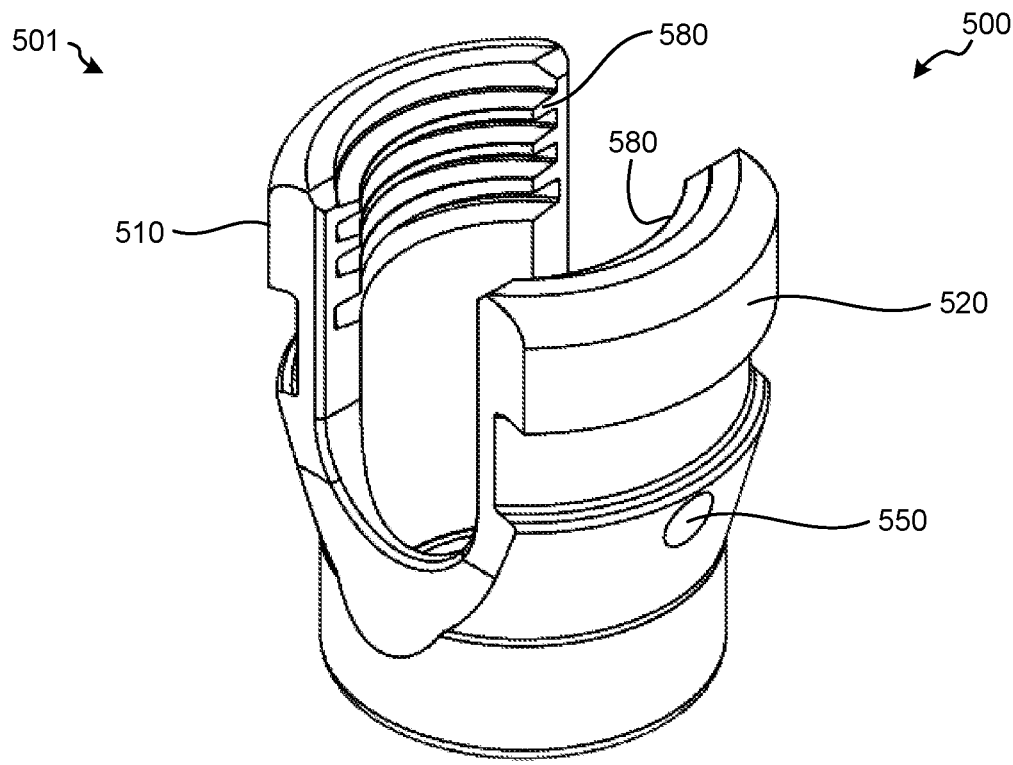
FIG. 5A is a top perspective view of a tulip member 500, according to an embodiment of the present disclosure.
Figure 5B:
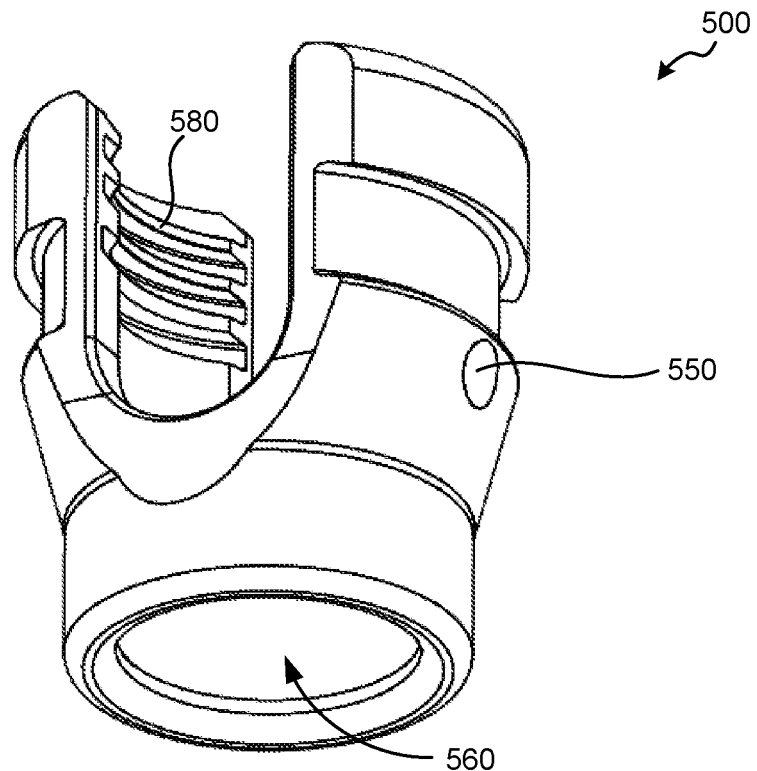
FIG. 5B is a bottom perspective view of the tulip member 500 of FIG. 5A.
Figure 5C:
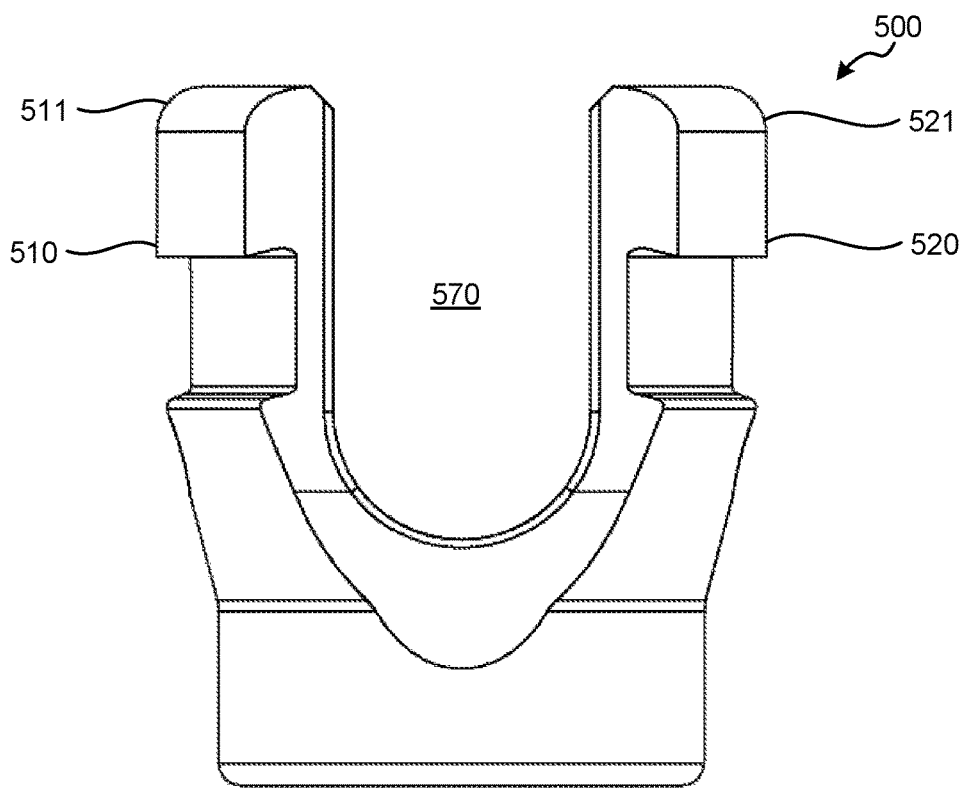
FIG. 5C is a front side view of the tulip member 500 of FIG. 5A.
Figure 5D:
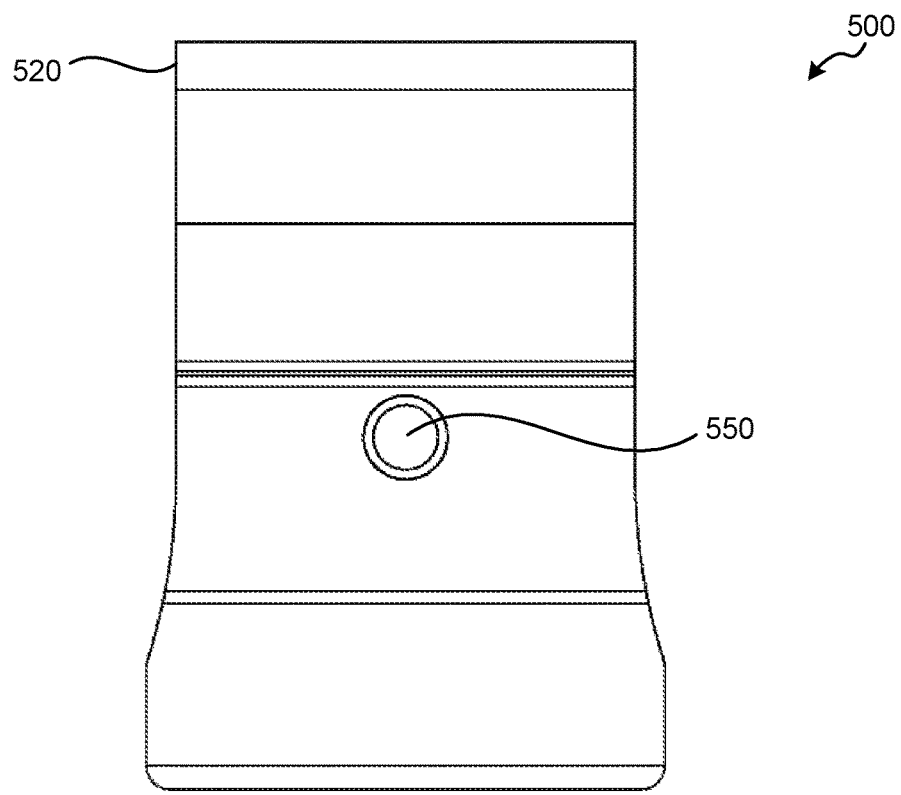
FIG. 5D is a left side view of the tulip member 500 of FIG. 5A.
Figure 5E:
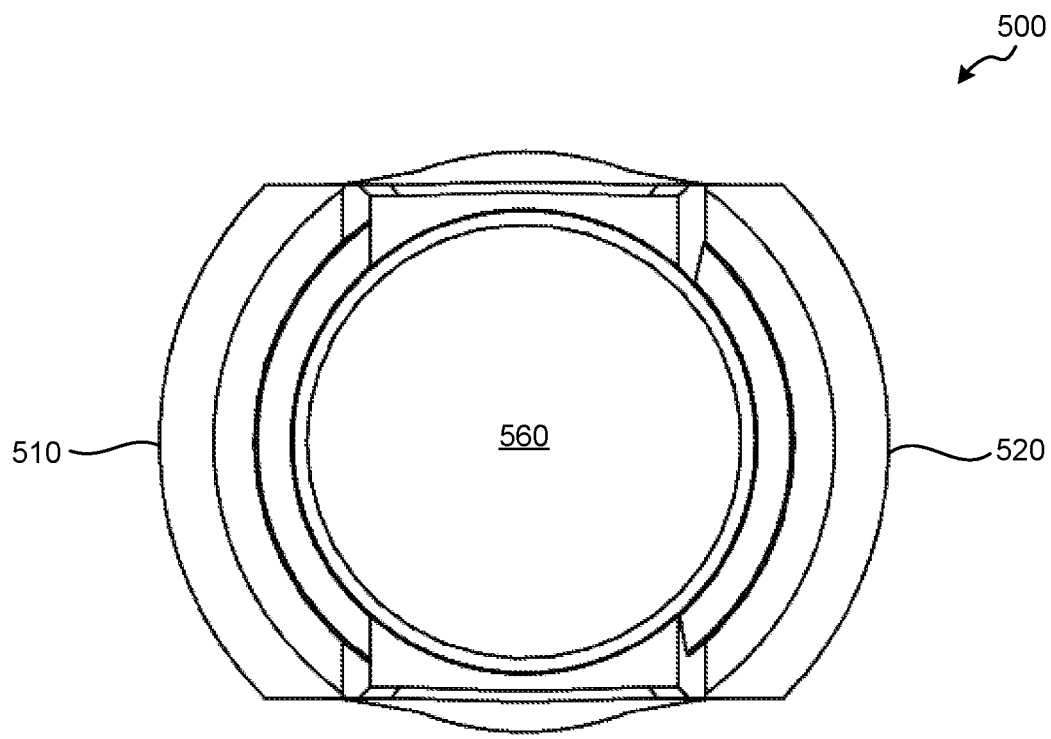
FIG. 5E is a top view of the tulip member 500 of FIG. 5A.
Figure 5F:
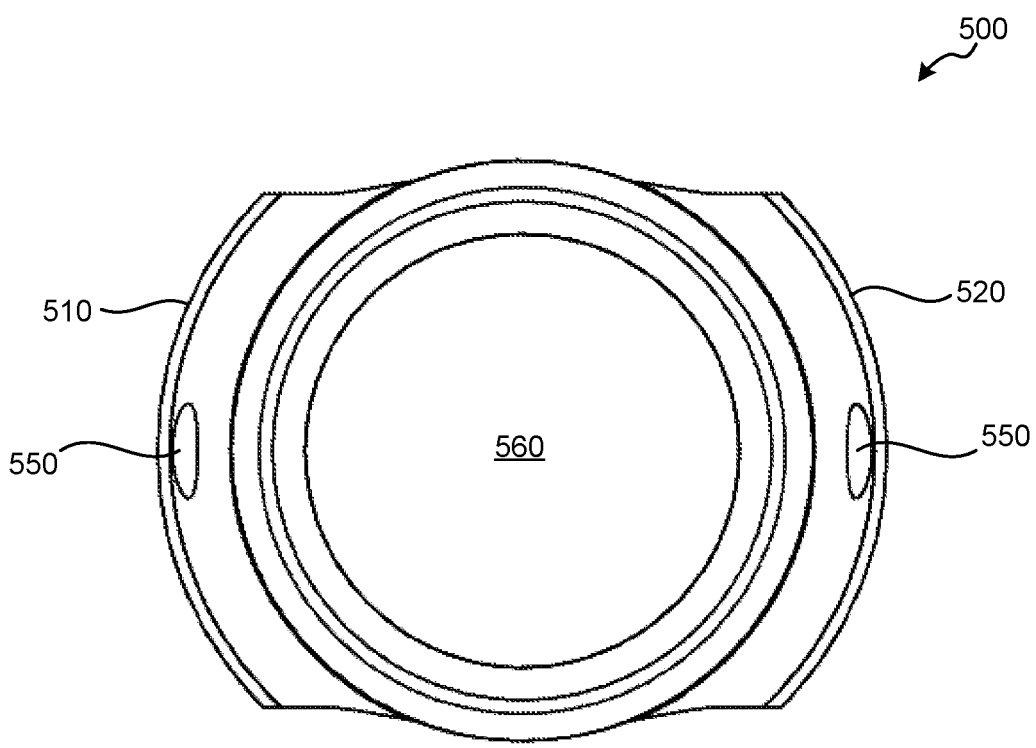
FIG. 5F is a bottom view of the tulip member 500 of FIG. 5A.

FIGS. 5A-5F illustrate various views of a tulip member 500, according to an embodiment of the present disclosure. Specifically, FIG. 5A is a top perspective view of the tulip member 500; FIG. 5B is a bottom perspective view of the tulip member 500; FIG. 5C is a front side view of the tulip member 500; FIG. 5D is a left side view of the tulip member 500; FIG. 5E is a top view of the tulip member 500; and FIG. 5F is a bottom view of the tulip member 500. The tulip member 500 may generally include a posterior end 501, an anterior end 502, an internal bore 560, a first tulip arm 510, a second tulip arm 520, and a transverse channel 570 formed between the first and second tulip arms 510, 520.

The first and second tulip arms 510, 520 may each be located proximate to and/or project from the posterior end 501 of the tulip member 500. The first and second tulip arms 510, 520 may be located on opposite sides of the posterior end 501 of the tulip member 500 such that a transverse channel 570 is formed between the first and second tulip arms 510, 520. In at least one embodiment, the first and second tulip arms 510, 520 may be rigid. Alternatively, in other embodiments the first and second tulip arms 510, 520 may be resilient such that they may bend and flex away from each other when a force is applied to the first and second tulip arms 510, 520. The first and second tulip arms 510, 520 may additionally include threading 580 formed in the posterior ends 511, 521 of the first and second tulip arms 510, 520. The threading 580 may be configured to receive a set screw, as will be discussed in more detail with respect to FIGS. 11A-13.

The internal bore 560 of the tulip member 500 may extend through the tulip member 500 between the posterior and anterior ends 501, 502 of the tulip member 500. The internal bore 560 may be configured to receive the collar member 300 therein. The internal bore 560 may also be configured to receive a driver tool therethrough, as will be discussed with respect to FIGS. 7A and 7B.

The tulip member 500 may additionally include tulip depressions 550 formed in the sides of the tulip member 500 proximate the first and second tulip arms 510, 520. The tulip depressions 550 may interact with the collar depressions 350 formed in the collar member 300 to couple the tulip member 500 to the collar member 300, as shown in FIGS. 7A and 7B. This coupling may be accomplished by inserting the collar member 300 into the internal bore 560 of the tulip member 500, aligning the tulip depressions 550 with the collar depressions 350, inserting a crimping tool (not shown) into the tulip depressions 550, and applying a crimping force to the tulip depressions 550 with the crimping tool in order to deform the tulip depressions 550 toward each other and into the collar depressions 350. In this manner, the deformed material of the crimped tulip depressions 550 will project inside the collar depressions 350 and couple the collar member 300 to the tulip member 500.

Figure 6A:
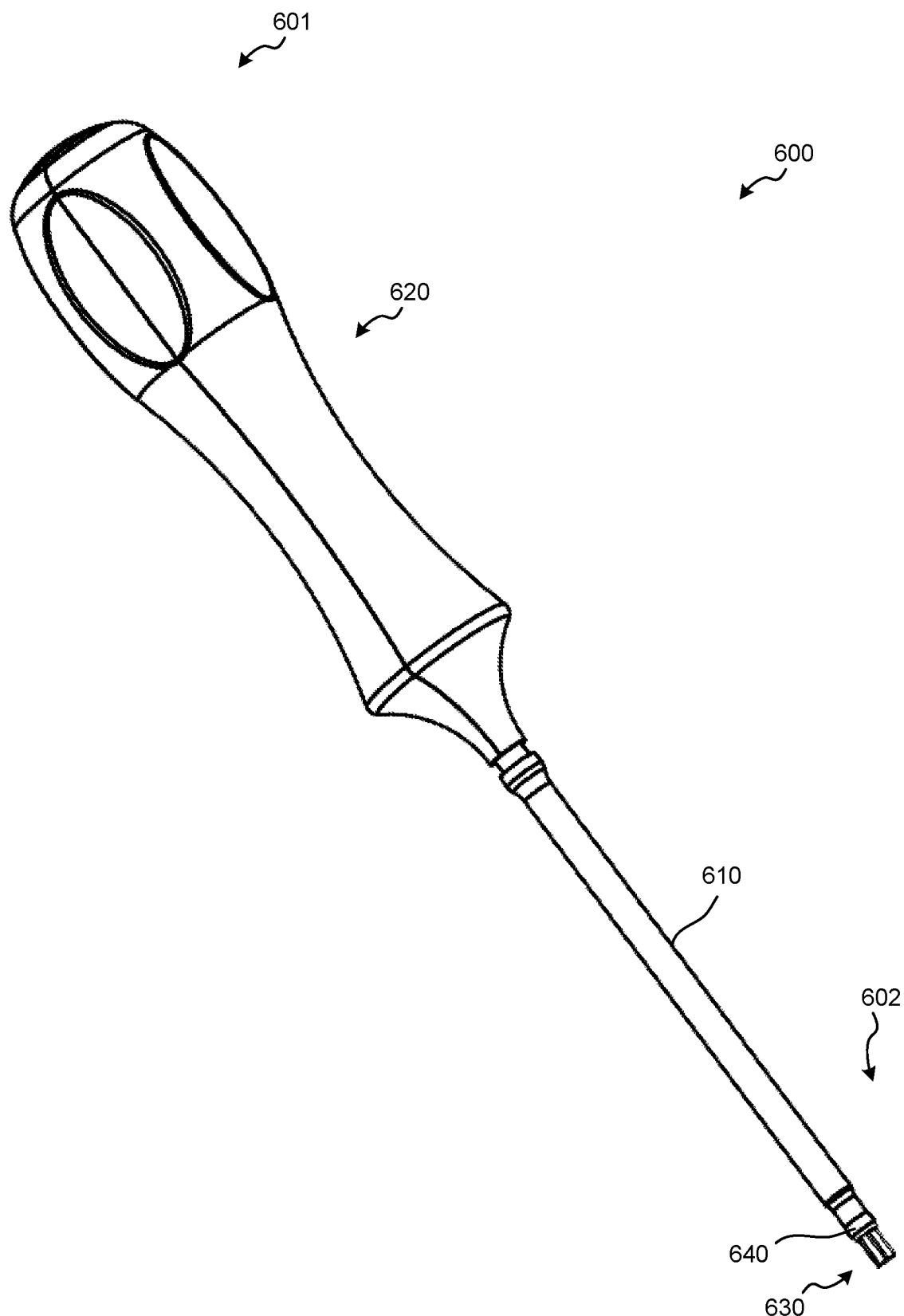
FIG. 6A is a perspective view of a driver tool 600, according to an embodiment of the present disclosure.
Figure 6D:
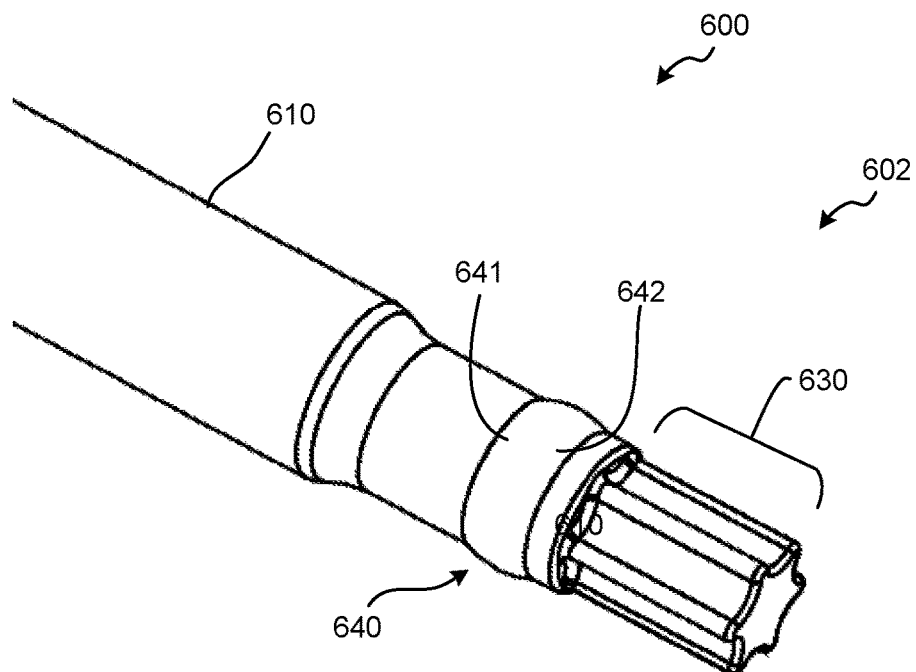
FIG. 6D is a perspective view of the distal end of the driver tool 600 of FIG. 6A.
Figure 6E:
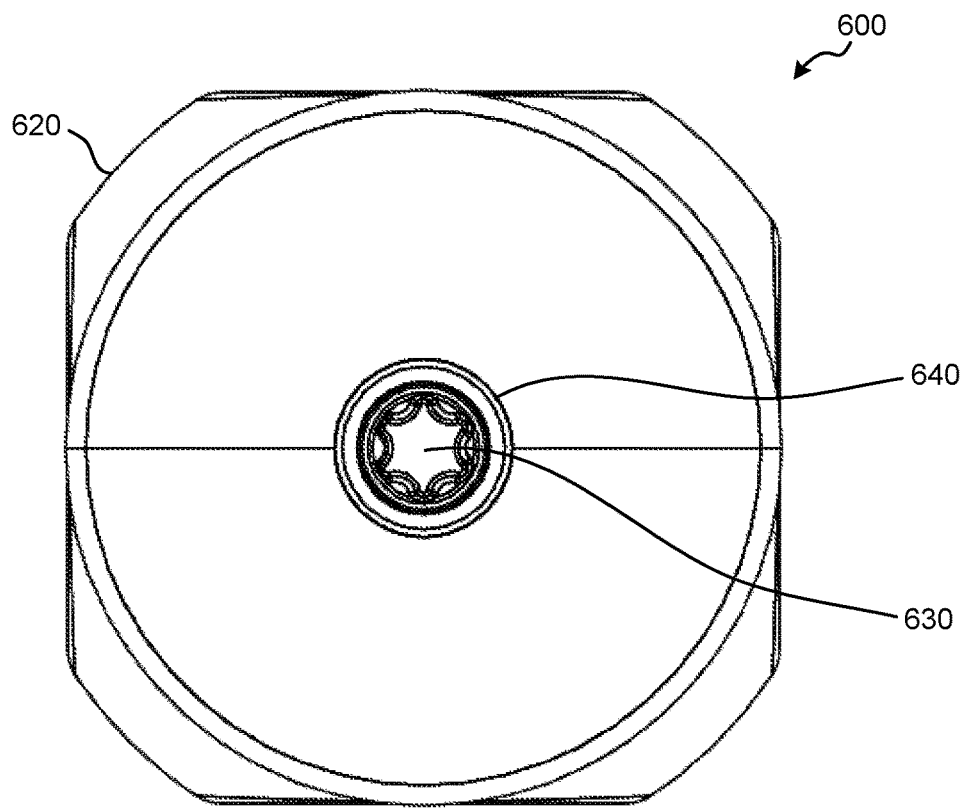
FIG. 6E a bottom view of the driver tool 600 of FIG. 6A.

FIGS. 6A-6F illustrate various views of a driver tool 600, according to an embodiment of the present disclosure. Specifically, FIG. 6A is a perspective view of the driver tool 600; FIG. 6B is a left side view of the driver tool 600; FIG. 6C is a right side view of the driver tool 600; FIG. 6D is a perspective view of the distal end of the driver tool 600; and FIG. 6E a bottom view of the driver tool 600. The driver tool 600 may generally include an elongate shaft 610 having a proximal end 601 and a distal end 602, a bone screw engagement feature 630 located at the distal end 602 of the elongate shaft 610, a handle 620 located at the proximal end 601 of the elongate shaft 610, and a retention feature 640.

The bone screw engagement feature 630 may be engageable with the driver engagement feature 240 formed in the bone screw head 230 in order to facilitate rotation of the bone screw 200 with the driver tool 600. In at least one embodiment, the bone screw engagement feature 630 may have an external hexalobular shape that is complementary to the internal hexalobular shape formed in the bone screw head 230. However, it will be understood that any suitable size, shape, or style of bone screw engagement feature 630 and/or driver engagement feature 240 may also be used in conjunction with the teachings of the present disclosure.

The retention feature 640 may be located proximate the bone screw engagement feature 630, located along the elongate shaft proximal to the bone screw engagement feature 630, and/or located intermediate the bone screw engagement feature 630 and the proximal end 601 of the elongate shaft 610. In at least one embodiment, the retention feature 640 may comprise a protrusion 640 encircling at least a portion of the elongate shaft 610. The protrusion 640 may have a semispherical shape with an anterior surface 642, a posterior surface 641, and a medial line (e.g., an equatorial line; not shown in FIG. 6D) intermediate the posterior and anterior surfaces 641, 642. In this manner, the protrusion 640 may be shaped to be retained between the first retaining arm 310 and the second retaining arm 320 of the collar member 300 of the bone anchor assembly 100. In a particular embodiment, the posterior surface 641 of the protrusion 640 may be shaped to be retained between the first retaining tab 315 located on the first retaining arm 310 of the collar member 300, and the second retaining tab 325 (opposite the first retaining tab 315) located on the second retaining arm of the collar member 300, as will be discussed with reference to FIGS. 7A and 7B below.

FIGS. 7A and 7B illustrate a bone anchor system 700 including a driver tool 600 and a bone anchor assembly 100, both prior to coupling the driver tool 600 to the bone anchor assembly 100, and after the driver tool 600 has been coupled to the bone anchor assembly 100, respectively. In general, the retention feature 640 is configured to removably couple the driver tool 600 to the bone anchor assembly 100 as the bone screw engagement feature 630 is moved into engagement with the driver engagement feature 240 of the bone screw 200 in the bone anchor assembly 100.

In at least one embodiment, the driver tool 600 may be removably couplable to the bone anchor assembly 100 by inserting the retention feature 640 of the driver tool 600 between the first and second retaining arms 310, 320 of the collar member 300, such that the retention feature 640 is retained by the first and second retaining arms 310, 320 of the collar member 300.

In a particular embodiment, the first and second retaining tabs 315, 325 of the first and second retaining arms 310, 320 of the collar member 300 may be configured to engage the posterior surface 641 of the retention feature 640 to removably couplable the driver tool 600 to the bone anchor assembly 100 by inserting the retention feature 640 past the first and second retaining tabs 315, 325 and between the first and second retaining arms 310, 320 of the collar member 300, such that the retention feature 640 is retained by the first and second retaining tabs 315, 325 and/or the first and second retaining arms 310, 320. This coupling procedure will be discussed in more detail with respect to FIGS. 14A-14B below.

Figure 8:
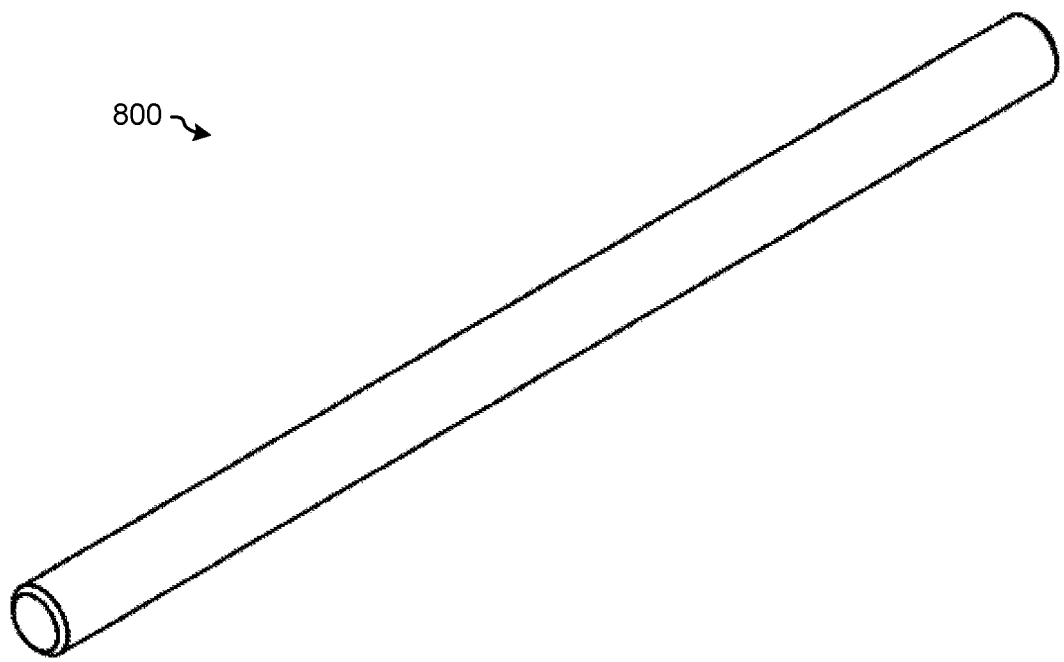
FIG. 8 is a perspective view of a straight connecting rod 800, according to an embodiment of the present disclosure.
Figure 9:
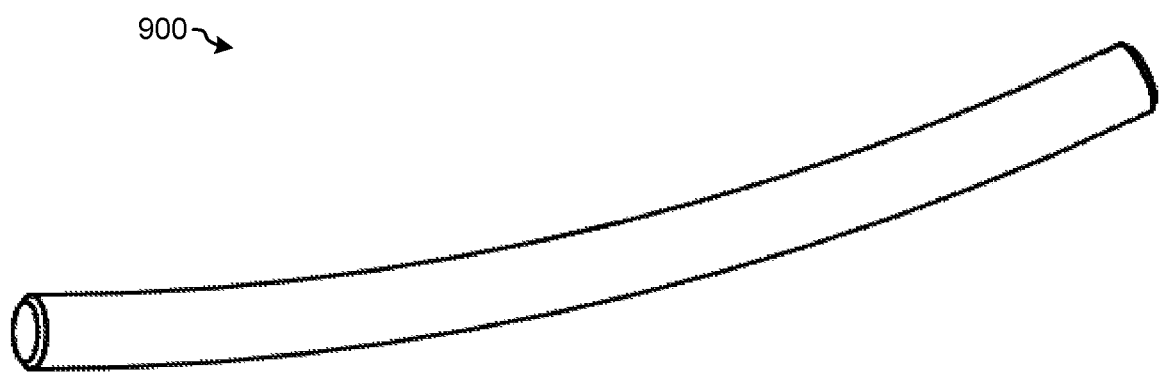
FIG. 9 is a perspective view of a curved connecting rod 900, according to an embodiment of the present disclosure.
Figure 10:
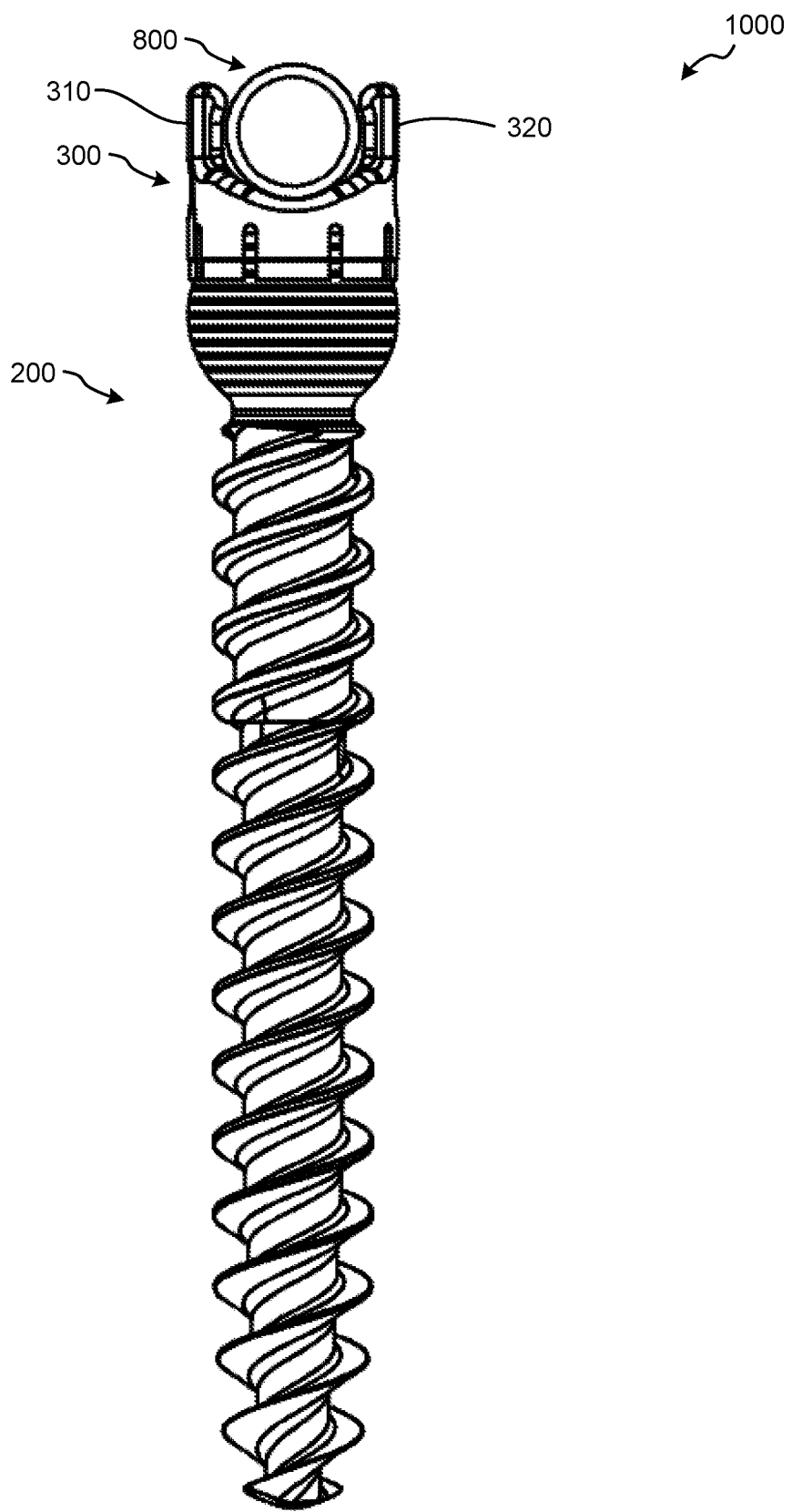
FIG. 10 is a front side view of a partial bone anchor assembly 1000 including the bone screw 200 of FIG. 2A, the collar member 300 of FIG. 3A, and the straight connecting rod 800 of FIG. 8.

FIGS. 8 and 9 illustrate perspective views of an example straight connecting rod 800 and an example curved connecting rod 900, respectively, each of which may be used in conjunction with the bone anchor assemblies of the present disclosure. However, it will be understood that other connecting rods of any suitable size, shape, or style may also be used in conjunction with the bone anchor assemblies disclosed herein. FIG. 10 shows a front side view of a partial bone anchor assembly 1000 including a bone screw 200, a collar member 300, and a straight connecting rod 800. In this manner, the first and second retaining arms 310, 320 of the collar member 300 may also be configured to provisionally retain a connecting rod 800 therebetween during assembly of the partial bone anchor assembly 1000, in order to facilitate the implantation process.

Figure 11A:
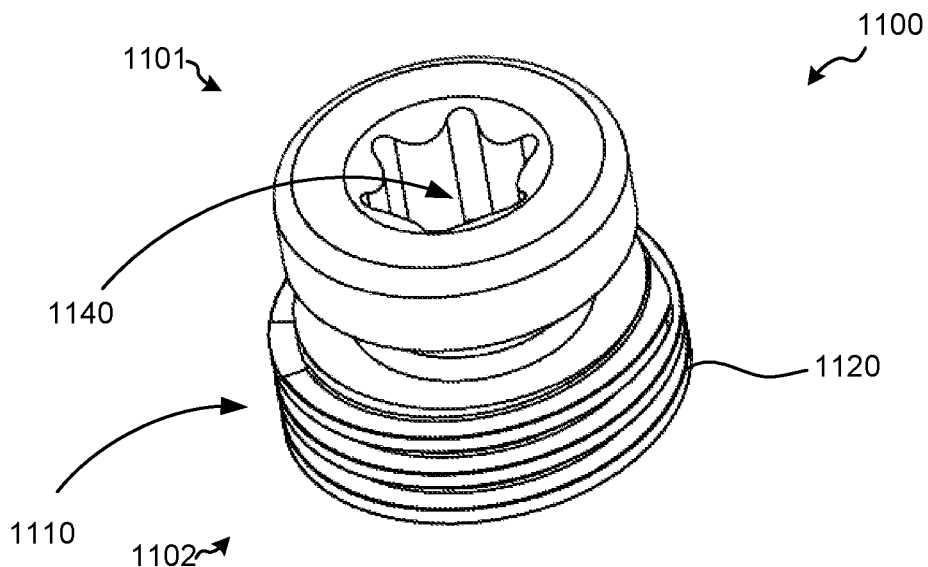
FIG. 11A is a top perspective view of a set screw 1100, according to an embodiment of the present disclosure.
Figure 11B:
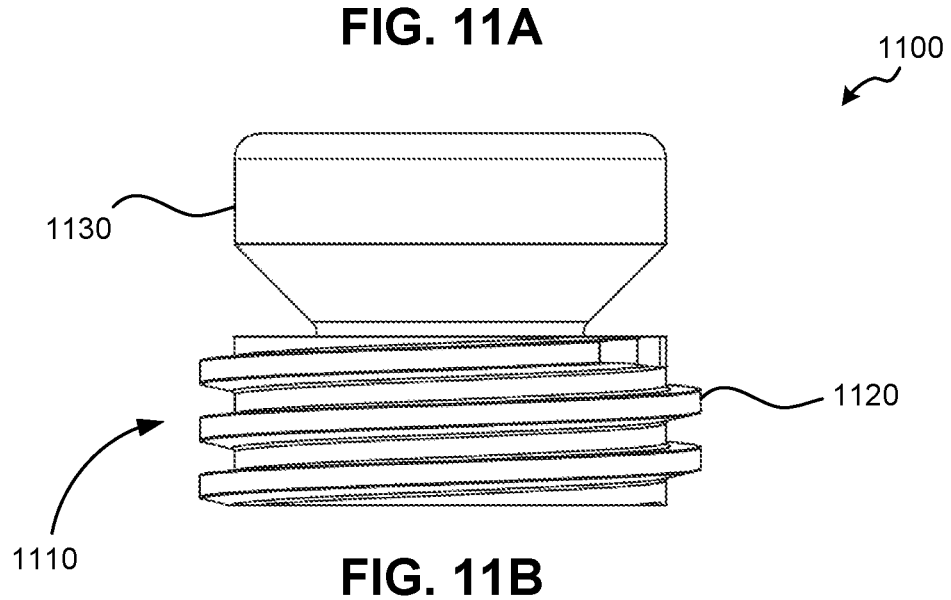
FIG. 11B is a side view of the set screw 1100 of FIG. 11A.
Figure 11C:
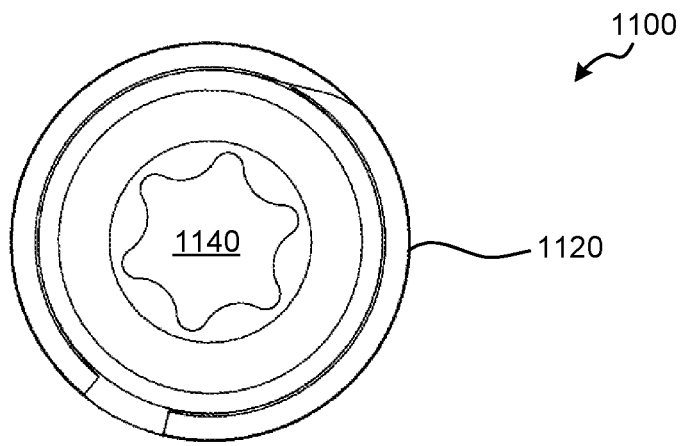
FIG. 11C is a top view of the set screw 1100 of FIG. 11A.

FIGS. 11A-11C illustrate various views of a set screw 1100, according to an embodiment of the present disclosure, which may be used in conjunction with the bone anchor assemblies disclosed herein. Specifically, FIG. 11A is a top perspective view of the set screw 1100; FIG. 11B is a side view of the set screw 1100; and FIG. 11C is a top view of the set screw 1100. In general, the set screw 1100 may include a proximal end 1101, a distal end 1102, a set screw body 1110 located toward the distal end 1102 of the set screw 1100, a set screw head 1130 located toward the proximal end 1101 of the set screw 1100, a set screw driver engagement feature 1140 formed in the set screw head 1130 and/or formed in the set screw body 1110, and set screw threading 1120 arranged about the set screw body 1110.

Figure 12:
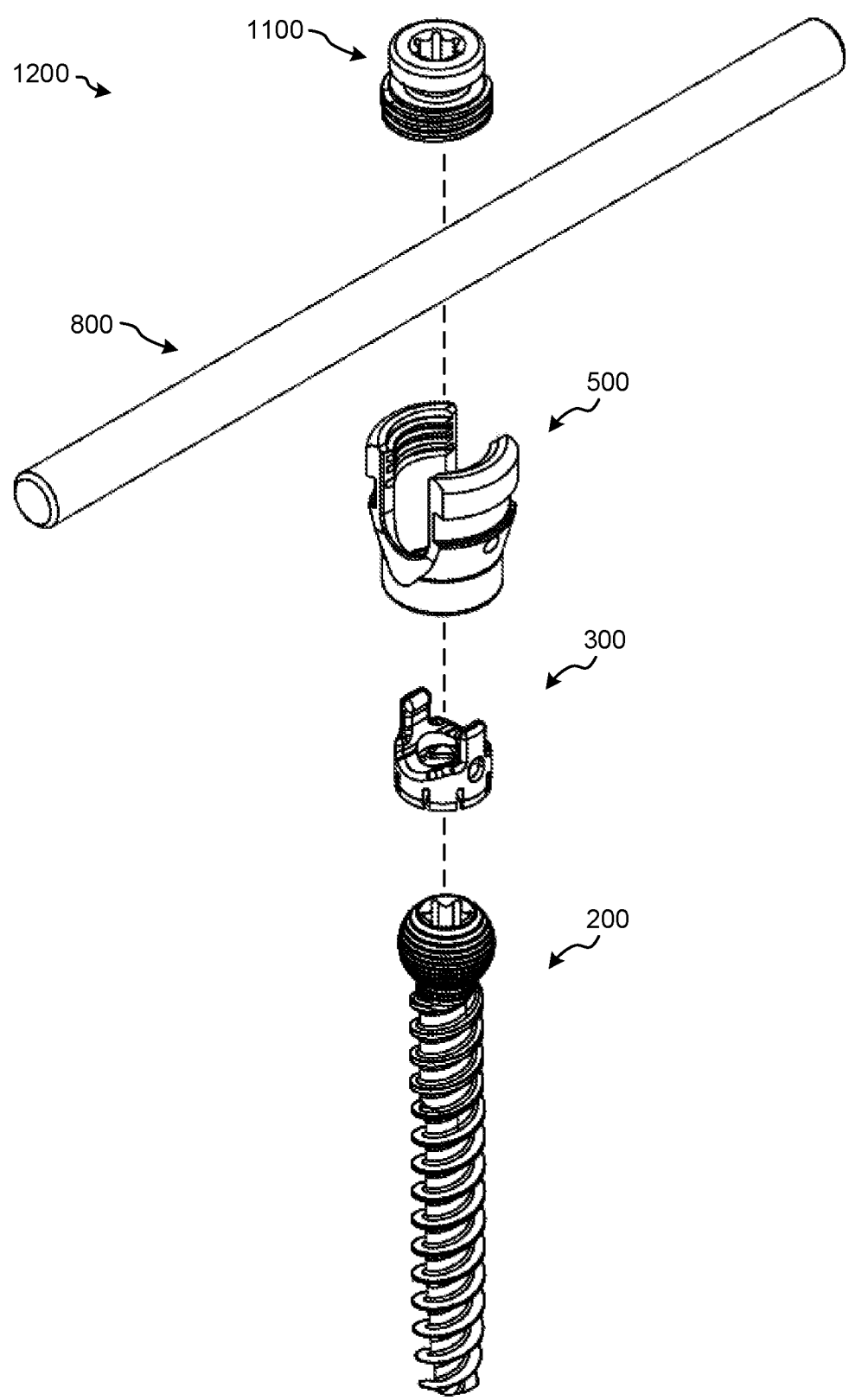
FIG. 12 is an exploded view of a bone anchor assembly 1200, according to an embodiment of the present disclosure.
Figure 13:
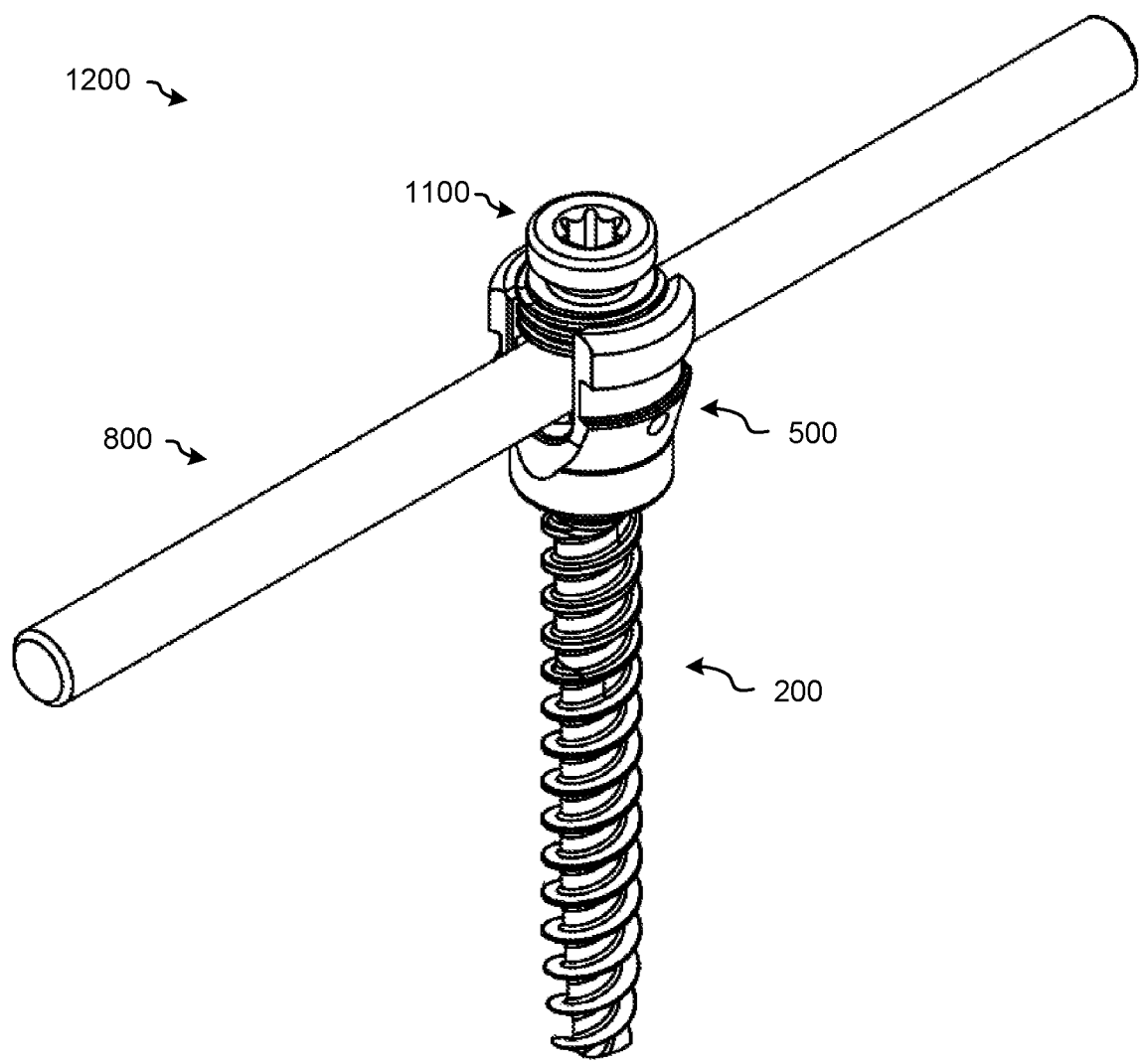
FIG. 13 is a perspective view of the bone anchor assembly 1200 of FIG. 12, fully assembled.

The set screw 1100 may be configured to engage the threading 580 of the first and second tulip arms 510, 520 in order to rigidly couple the connecting rod 800 to the bone anchor assembly 1200. This is best seen in FIGS. 12 and 13, which respectively show an exploded view of the bone anchor assembly 1200 (including the connecting rod 800 and the set screw 1100), and an assembled view of the bone anchor assembly 1200.

In at least one embodiment, the set screw head 1130 may be further designed to shear off from the set screw body 1110 (not shown) when a torque force of sufficient magnitude is applied to the set screw head 1130, relative to the set screw body 1110, during the process of rigidly coupling the connecting rod 800 to the bone anchor assembly 1200 via the set screw 1100.

Figure 14A:
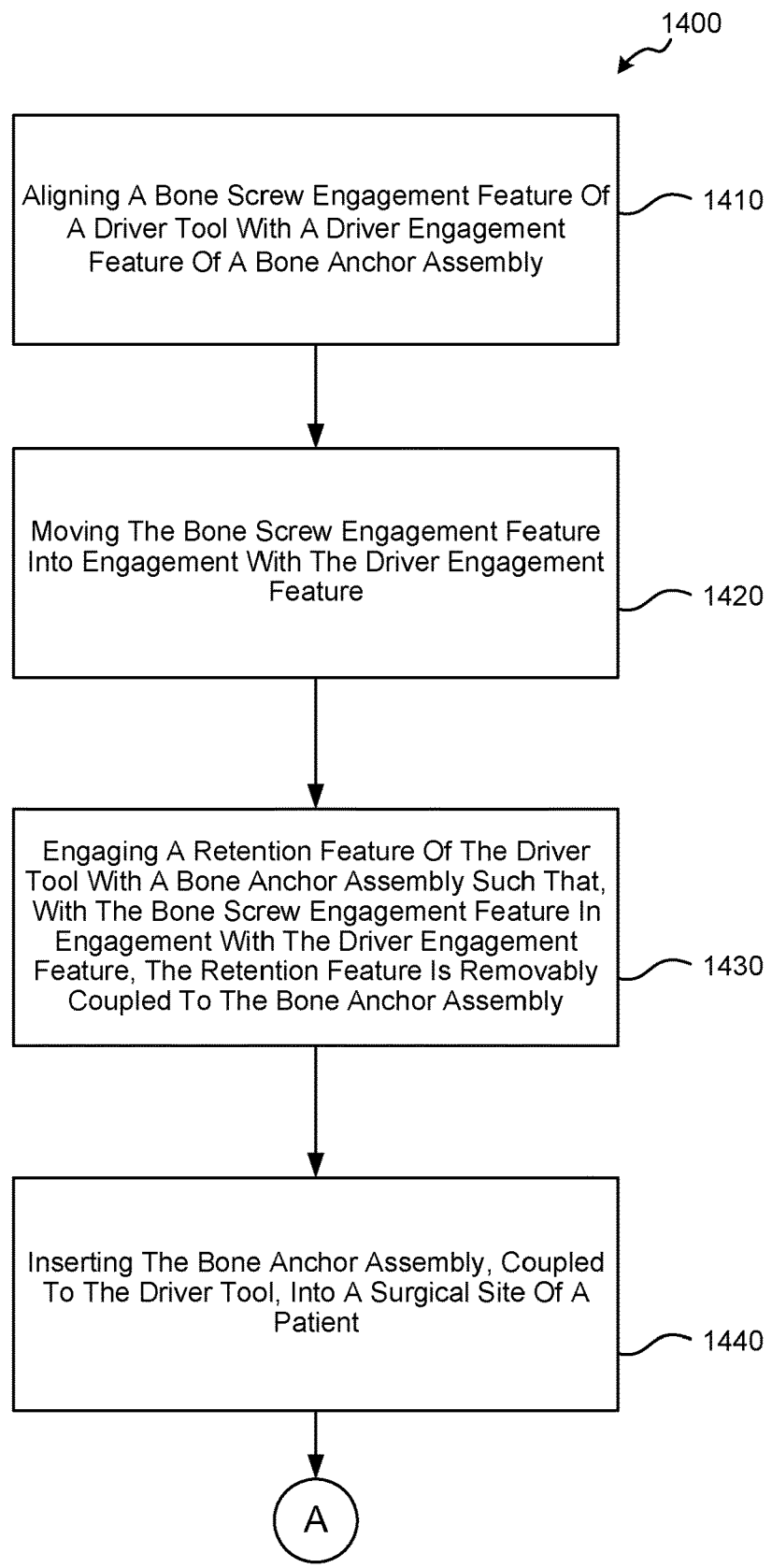
FIGS. 14A-B illustrate a flowchart of a method 1400 for implanting a bone anchor assembly, according to an embodiment of the present disclosure.
Figure 14B:
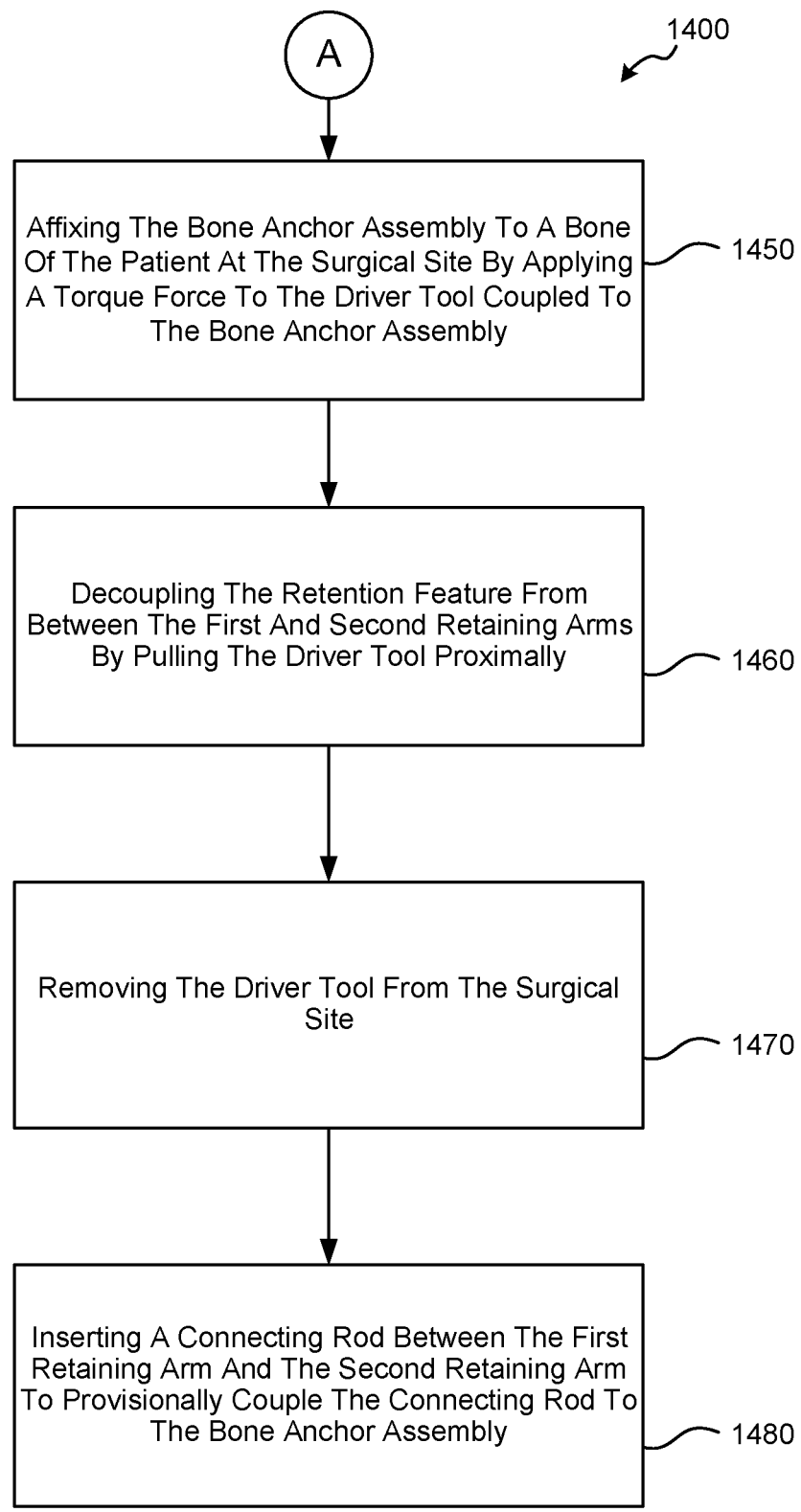

FIGS. 14A-B illustrate a flowchart of a method 1400 for implanting a bone anchor assembly, according to an embodiment of the present disclosure. In general, the method 1400 may include use of a driver tool comprising an elongate shaft having a proximal end, a distal end, a bone screw engagement feature located at the distal end of the elongate shaft, and a retention feature that is located proximal the bone screw engagement feature. The method 1400 may also utilize a bone anchor assembly comprising a driver engagement feature.

The method 1400 may begin with a step 1410 in which the bone screw engagement feature of the driver tool may be aligned with the driver engagement feature of the bone anchor assembly. In at least one embodiment, the driver engagement feature may be formed in a bone screw of the bone anchor assembly.

Once the bone screw engagement feature of the driver tool has been aligned with the driver engagement feature of the bone anchor assembly, the method 1400 may proceed to a step 1420 in which the bone screw engagement feature of the driver tool may be moved into engagement with the driver engagement feature of the bone anchor assembly.

Once the bone screw engagement feature of the driver tool has been moved into engagement with the driver engagement feature of the bone anchor assembly, the method 1400 may proceed to a step 1430 in which the retention feature of the driver tool may be engaged with the bone anchor assembly such that, with the bone screw engagement feature in engagement with the driver engagement feature, the retention feature may be removably coupled to the bone anchor assembly.

In a particular embodiment, the retention feature may comprise a semispherical shape having an anterior surface and a posterior surface and the bone anchor assembly may comprise a first retaining arm having a first retaining tab and a second retaining arm having a second retaining tab, opposite the first retaining tab. In this embodiment, engaging the retention feature with the bone anchor assembly may further include: (1) engaging the anterior surface of the retention feature with the first and second retaining tabs; (2) applying an insertion force to the retention feature, relative to the first and second retaining tabs, sufficient to cause the first and second retaining arms to deflect away from each other and permit the retention feature to enter a space formed between the first and second retaining arms; and (3) inserting the retention feature between the first and second retaining arms to engage the first and second retaining tabs with the posterior surface of the retention feature and couple the driver tool to the bone anchor assembly.

Once the retention feature of the driver tool has be engaged with the bone anchor assembly to removably couple the driver tool to the bone anchor assembly, the method 1400 may proceed to a step 1440 in which the bone anchor assembly (coupled to the driver tool) may be inserted into a surgical site of a patient, and the method 1400 may end. Alternatively, or in addition thereto, the method 1400 may proceed to any or all of steps 1450-1480, as will be discussed below.

Once the bone anchor assembly (coupled to the driver tool) has been inserted into the surgical site of the patient, the method 1400 may proceed to a step 1450 in which the bone anchor assembly may be affixed to a bone of the patient at the surgical site by applying a torque force to the driver tool coupled to the bone anchor assembly.

Once the bone anchor assembly has been affixed to the bone of the patient, the method 1400 may proceed to a step 1460 in which the retention feature of the driver tool may be decoupled from between the first and second retaining arms of the bone anchor assembly by pulling the driver tool proximally.

In a particular embodiment, decoupling the retention feature of the driver tool from between the first and second retaining arms of the bone anchor assembly may include: (1) engaging the posterior surface of the retention feature with the first and second retaining tabs; (2) applying a decoupling force to the retention feature, relative to the first and second retaining tabs, sufficient to cause the first and second retaining arms to deflect away from each other and permit the retention feature to exit the space formed between the first and second retaining arms; and (3) decoupling the retention feature from between the first and second retaining arms by pulling the driver tool proximally.

Once the retention feature of the driver tool has been decoupled from between the first and second retaining arms of the bone anchor assembly, the method 1400 may proceed to a step 1470 in which the driver tool may be removed from the surgical site.

Once the driver tool has been removed from the surgical site, the method 1400 may proceed to a step 1480 in which a connecting rod may be inserted between the first retaining arm and the second retaining arm of the bone anchor assembly in order to provisionally couple the connecting rod to the bone anchor assembly, and the method 1400 may end.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A bone anchor system comprising:
   a bone anchor assembly comprising:

a bone screw comprising:
a shank;
external threading along the shank configured to engage bone; and
a bone screw head coupled to a proximal end of the shank, the bone screw head comprising a driver engagement feature;
a collar member comprising:
a posterior end;
an anterior end;
a first retaining arm projecting from the posterior end of the collar member;
a second retaining arm projecting from the posterior end of the collar member, opposite the first retaining arm;
a receptacle configured to receive the bone screw head at any of a range of relative orientations, about multiple orthogonal axes of rotation; and
a grip feature proximate the receptacle, the receptacle and grip feature configured to engage the bone screw head; and
a tulip member comprising:
a posterior end;
an anterior end;
an internal bore extending through the tulip member between the posterior end and the anterior end of the tulip member;
a first tulip arm proximate the posterior end of the tulip member;
a second tulip arm proximate the posterior end of the tulip member; and
a transverse channel formed between the first and second tulip arms; and
a driver tool comprising:
an elongate shaft having a proximal end and a distal end;
a bone screw engagement feature located at the distal end of the elongate shaft, wherein the bone screw engagement feature is engageable with the driver engagement feature of the bone screw head to facilitate rotation of the bone screw with the driver tool; and
a retention feature located proximate the bone screw engagement feature, wherein the driver tool is removably couplable to the bone anchor assembly by inserting the retention feature between the first and second retaining arms of the collar member, such that the first and second retaining arms flex to retain the retention feature.

2. The bone anchor system of claim 1, wherein the retention feature comprises a semispherical shape having an anterior surface and a posterior surface.

3. The bone anchor system of claim 2, wherein:
the first retaining arm further comprises a first retaining tab located on a posterior end of the first retaining arm; and
the second retaining arm further comprises a second retaining tab located on a posterior end of the second retaining arm, opposite the first retaining tab, the first and second retaining tabs configured to engage the posterior surface of the retention feature to removably couplable the driver tool to the bone anchor assembly by inserting the retention feature past the first and second retaining tabs and between the first and second retaining arms of the collar member such that the retention feature is retained by the first and second retaining arms.

4. The bone anchor system of claim 1, wherein the first retaining arm and the second retaining arm are resilient.

5. The bone anchor system of claim 1, wherein the grip feature comprises a collet structure.

6. The bone anchor system of claim 1, wherein the first and second retaining arms of the collar member are configured to provisionally retain a connecting rod.

7. The bone anchor system of claim 6, wherein:
the first and second tulip arms comprise threading; and
the bone anchor assembly further comprises a set screw configured to engage the threading of the first and second tulip arms and rigidly couple the connecting rod to the bone anchor assembly.

8. A driver tool comprising:
an elongate shaft having a proximal end and a distal end;
a bone screw engagement feature located at the distal end of the elongate shaft; and
a retention feature located along the elongate shaft, proximal to the bone screw engagement feature;
wherein the retention feature is configured to removably couple the driver tool to a bone anchor assembly, without deformation of the retention feature, in direct response to motion linear insertion of the bone screw engagement feature into engagement with a driver engagement feature of a bone screw of the bone anchor assembly.

9. The driver tool of claim 8, wherein the retention feature comprises a protrusion encircling at least a portion of the elongate shaft.

10. The driver tool of claim 9, wherein the protrusion comprises a semispherical shape.

11. The driver tool of claim 10, wherein the protrusion comprises:
an anterior surface;
a posterior surface; and
a medial line intermediate the anterior and posterior surfaces.

12. The driver tool of claim 11, wherein the protrusion is shaped to be retained between a first retaining arm and a second retaining arm of the bone anchor assembly.

13. The driver tool of claim 12, wherein the posterior surface of the protrusion is shaped to be retained by a first retaining tab located on the first retaining arm and a second retaining tab located on the second retaining arm, opposite the first retaining tab.

14. The driver tool of claim 8, wherein the retention feature is intermediate the bone screw engagement feature and the proximal end of the elongate shaft.

15. The bone anchor assembly of claim 8, wherein the retention feature has a first width, perpendicular to the elongate shaft, that is greater than a second width, perpendicular to the elongate shaft, at a portion of the elongate shaft immediately proximal to the retention feature.

16. The bone anchor assembly of claim 8, wherein the retention feature comprises an unbroken circular cross-sectional shape.

17. A bone anchor system comprising:
a bone anchor assembly comprising:
a bone screw comprising:
a shank;
external threading along the shank configured to engage bone; and
a bone screw head coupled to a proximal end of the shank, the bone screw head comprising a driver engagement feature;
a collar member comprising:
a posterior end;

an anterior end;
a first retaining arm projecting from the posterior end of the collar member;
a second retaining arm projecting from the posterior end of the collar member, opposite the first retaining arm;
a receptacle configured to receive the bone screw head at any of a range of relative orientations, about multiple orthogonal axes of rotation; and
a grip feature proximate the receptacle, the receptacle and grip feature configured to engage the bone screw head; and
a tulip member comprising:
a posterior end;
an anterior end;
an internal bore extending through the tulip member between the posterior end and the anterior end of the tulip member;
a first tulip arm proximate the posterior end of the tulip member;
a second tulip arm proximate the posterior end of the tulip member; and
a transverse channel formed between the first and second tulip arms;
a rod; and
a driver tool comprising:
an elongate shaft having a proximal end and a distal end;
a bone screw engagement feature located at the distal end of the elongate shaft, wherein the bone screw engagement feature is engageable with the driver engagement feature of the bone screw head to facilitate rotation of the bone screw with the driver tool; and
a retention feature located proximate the bone screw engagement feature;
wherein the first retaining arm and the second retaining arm are configured to provisionally retain the retention feature, and are configured to provisionally retain the rod.

18. The bone anchor system of claim 17, wherein:
the first retaining arm and the second retaining arm are configured to flex apart to provisionally retain the rod; and
with the rod provisionally retained by the collar, the first retaining arm and the second retaining arm extend beyond a central axis of the rod.

19. A bone anchor system comprising:
a bone anchor assembly comprising a bone screw;
a rod; and
a driver tool comprising:
an elongate shaft having a proximal end and a distal end;
a bone screw engagement feature located at the distal end of the elongate shaft; and
a retention feature located along the elongate shaft, proximal to the bone screw engagement feature;
wherein:
the bone screw engagement feature is configured to engage the bone screw; and
the bone anchor assembly comprises a collar configured to provisionally retain the retention feature and configured to provisionally retain the rod.

20. The bone anchor system of claim 19, wherein:
the bone anchor assembly comprises a collar member comprising:
a posterior end;
an anterior end;
a first retaining arm projecting from the posterior end of the collar member;
a second retaining arm projecting from the posterior end of the collar member, opposite the first retaining arm;
the retention feature comprises a convex semispherical shape; and
the first retaining arm and the second retaining arm are configured to flex apart to receive the convex semispherical shape to removably couple the driver tool to the bone anchor assembly.

21. A bone anchor system comprising:
a bone anchor assembly comprising a bone screw; and
a driver tool comprising:
an elongate shaft having a proximal end and a distal end;
a bone screw engagement feature located at the distal end of the elongate shaft; and
a retention feature located along the elongate shaft, proximal to the bone screw engagement feature;
wherein:
the bone screw engagement feature is configured to engage the bone screw; and
the retention feature comprises a convex semispherical shape, with an unbroken circular cross-sectional shape, that is receivable by the bone anchor assembly to contact the bone anchor to removably couple the driver tool to the bone anchor assembly.

22. The bone anchor assembly of claim 21, wherein the bone anchor assembly comprises:
a tulip member comprising:
a first tulip arm;
a second tulip arm; and
a collar member positionable between the first tulip arm and the second tulip arm, the collar member comprising:
a first retaining arm;
a second retaining arm;
a rod; and
a monolithic set screw comprising:
a set screw head comprising a driver engagement feature; and
a set screw body, threadably engageable with the first tulip arm and the second tulip arm such that, with the rod positioned between the first retaining arm and the second retaining arm, the set screw body contacts the rod.

23. A driver tool comprising:
an elongate shaft having a proximal end and a distal end;
a bone screw engagement feature located at the distal end of the elongate shaft; and
a retention feature located along the elongate shaft, proximal to the bone screw engagement feature;
wherein the retention feature is configured to removably couple the driver tool to a bone anchor assembly, without deformation of the retention feature and without rotation of the retention feature relative to the bone screw engagement feature, as the bone screw engagement feature is moved into engagement with a driver engagement feature of a bone screw of the bone anchor assembly.

24. The driver tool of claim 16, wherein the engagement feature is in a fixed position relative to the bone screw engagement feature.

* * * * *